United States Patent
Warren et al.

(10) Patent No.: US 10,166,056 B2
(45) Date of Patent: Jan. 1, 2019

(54) METHOD AND APPARATUS FOR SACROILIAC JOINT FIXATION

(71) Applicant: DePuy Synthes Products, Inc., Raynham, MA (US)

(72) Inventors: Christopher R. Warren, Trabuco Canyon, CA (US); Robert J. Flower, Sun City, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/348,177

(22) Filed: Nov. 10, 2016

(65) Prior Publication Data

US 2017/0151005 A1  Jun. 1, 2017

Related U.S. Application Data

(63) Continuation of application No. 14/030,391, filed on Sep. 18, 2013, now Pat. No. 9,522,028.

(60) Provisional application No. 61/842,664, filed on Jul. 3, 2013.

(51) Int. Cl.
*A61B 17/86* (2006.01)
*A61B 17/88* (2006.01)

(52) U.S. Cl.
CPC ........ *A61B 17/8685* (2013.01); *A61B 17/864* (2013.01); *A61B 17/8625* (2013.01); *A61B 17/8805* (2013.01); *A61B 2017/8655* (2013.01)

(58) Field of Classification Search
CPC ............ A61B 17/8625; A61B 17/8685; A61B 17/844; A61B 2017/8655
See application file for complete search history.

(56) References Cited

U.S. PATENT DOCUMENTS

| | | |
|---|---|---|
| 2,077,804 A | 4/1937 | Morrison |
| 2,121,193 A | 6/1938 | Hanicke |
| 2,381,050 A | 8/1945 | Hardinge |
| 2,388,056 A | 10/1945 | Hendricks |
| 2,485,531 A | 10/1949 | William et al. |
| 2,489,870 A | 11/1949 | Dzus |
| 2,570,465 A | 10/1951 | Lundholm |
| 3,115,804 A | 12/1963 | Johnson |

(Continued)

FOREIGN PATENT DOCUMENTS

| | | |
|---|---|---|
| DE | 19832798 C1 | 11/1999 |
| DE | 20101793 U1 | 5/2001 |

(Continued)

OTHER PUBLICATIONS

May 27, 2009 Office Action for Japanese Patent Application No. 2005-50552 filed on Jul. 18, 2003.

(Continued)

*Primary Examiner* — Andrew Yang
(74) *Attorney, Agent, or Firm* — Baker & Hostetler LLP

(57) ABSTRACT

Disclosed is a fixation device for sacroiliac joint stabilization. The fixation device includes an elongated body comprising a bone anchor at a distal end. An axially moveable proximal anchor is carried by the proximal end of the fixation device. In one embodiment, the device is inserted through the ilium of the pelvis and the bone anchor is rotated into position within the sacrum. The proximal anchor is distally advanced with respect to the bone anchor to provide compression across the sacroiliac joint.

23 Claims, 32 Drawing Sheets

(56) References Cited

U.S. PATENT DOCUMENTS

| | | |
|---|---|---|
| 3,489,143 A | 1/1970 | Halloran |
| 3,678,925 A * | 7/1972 | Fischer ............... A61B 17/742 606/68 |
| 3,698,391 A | 10/1972 | Mahony |
| 4,052,988 A | 10/1977 | Doddi et al. |
| 4,175,555 A | 11/1979 | Herbert |
| 4,275,717 A | 6/1981 | Bolesky |
| 4,456,005 A | 6/1984 | Lichty |
| 4,463,753 A | 8/1984 | Gustilo |
| 4,532,660 A | 8/1985 | Field |
| 4,632,101 A | 12/1986 | Freedland |
| 4,640,271 A | 2/1987 | Lower |
| 4,646,741 A | 3/1987 | Smith |
| 4,667,663 A | 5/1987 | Miyata |
| 4,688,561 A | 8/1987 | Reese |
| 4,721,103 A | 1/1988 | Freedland |
| 4,743,257 A | 5/1988 | Tormala et al. |
| 4,790,304 A | 12/1988 | Rosenberg |
| 4,796,612 A | 1/1989 | Reese |
| 4,827,917 A | 5/1989 | Brumfield |
| 4,873,976 A | 10/1989 | Schreiber |
| 4,889,119 A | 12/1989 | Jamiolkowski et al. |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,968,317 A | 11/1990 | Tormala et al. |
| 4,978,349 A | 12/1990 | Frigg |
| 5,059,193 A | 10/1991 | Kuslich |
| 5,062,849 A | 11/1991 | Schelhas |
| 5,092,891 A | 3/1992 | Stuchin |
| 5,098,241 A | 3/1992 | Aldridge et al. |
| 5,098,433 A | 3/1992 | Freedland |
| 5,116,336 A | 5/1992 | Frigg |
| 5,122,133 A | 6/1992 | Evans |
| 5,122,141 A | 6/1992 | Simpson et al. |
| 5,167,663 A | 12/1992 | Brumfield |
| 5,167,664 A | 12/1992 | Hodorek |
| 5,217,462 A | 6/1993 | Asnis et al. |
| 5,234,431 A | 8/1993 | Keller |
| 5,242,447 A | 9/1993 | Borzone |
| 5,246,441 A | 9/1993 | Ross et al. |
| 5,250,049 A | 10/1993 | Michael |
| 5,300,074 A | 4/1994 | Frigg |
| 5,334,184 A | 8/1994 | Bimman |
| 5,364,398 A | 11/1994 | Chapman et al. |
| 5,370,646 A | 12/1994 | Reese et al. |
| 5,370,647 A | 12/1994 | Graber et al. |
| 5,382,248 A | 1/1995 | Jacobson et al. |
| 5,387,213 A | 2/1995 | Breard et al. |
| 5,395,371 A | 3/1995 | Miller et al. |
| 5,415,661 A | 5/1995 | Holmes |
| 5,449,359 A | 9/1995 | Groiso |
| 5,452,748 A | 9/1995 | Simmons et al. |
| 5,470,333 A | 11/1995 | Ray |
| 5,496,318 A | 3/1996 | Howland et al. |
| 5,498,265 A | 3/1996 | Asnis et al. |
| 5,501,695 A | 3/1996 | Anspach, Jr. et al. |
| 5,520,690 A | 5/1996 | Errico et al. |
| 5,527,312 A | 6/1996 | Ray |
| 5,536,127 A | 7/1996 | Pennig |
| 5,540,688 A | 7/1996 | Navas |
| 5,545,164 A | 8/1996 | Howland |
| 5,549,610 A | 8/1996 | Russell et al. |
| 5,558,674 A | 9/1996 | Heggeness et al. |
| 5,569,248 A | 10/1996 | Mathews |
| 5,569,548 A | 10/1996 | Koike et al. |
| 5,591,168 A | 1/1997 | Judet et al. |
| 5,609,634 A | 3/1997 | Voydeville |
| 5,626,613 A | 5/1997 | Schmieding |
| 5,628,751 A | 5/1997 | Sander et al. |
| 5,645,599 A | 7/1997 | Samani |
| 5,649,931 A | 7/1997 | Bryant et al. |
| 5,662,683 A | 9/1997 | Kay |
| 5,667,508 A | 9/1997 | Errico et al. |
| 5,669,915 A | 9/1997 | Caspar et al. |
| 5,713,903 A | 2/1998 | Sander et al. |
| 5,720,753 A | 2/1998 | Sander et al. |
| 5,725,541 A | 3/1998 | Anspach, III et al. |
| 5,725,588 A | 3/1998 | Errico et al. |
| 5,728,097 A | 3/1998 | Mathews |
| 5,728,116 A | 3/1998 | Rosenman |
| 5,741,282 A | 4/1998 | Anspach, III et al. |
| 5,772,662 A | 6/1998 | Chapman et al. |
| 5,782,865 A | 7/1998 | Grotz |
| 5,810,821 A | 9/1998 | Vandewalle |
| 5,849,004 A | 12/1998 | Bramlet |
| 5,871,485 A | 2/1999 | Rao et al. |
| 5,893,850 A | 4/1999 | Cachia |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,924 A | 9/1999 | Tormala et al. |
| 5,968,044 A | 10/1999 | Nicholson et al. |
| 5,976,139 A | 11/1999 | Bramlet |
| 5,984,927 A | 11/1999 | Wenstrom, Jr. et al. |
| 5,984,966 A | 11/1999 | Kiema et al. |
| 5,989,255 A | 11/1999 | Pepper et al. |
| 5,993,459 A | 11/1999 | Larsen et al. |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,566 A | 12/1999 | Wenstrom, Jr. |
| 6,007,580 A | 12/1999 | Lehto et al. |
| 6,010,513 A | 1/2000 | Tormala et al. |
| 6,015,410 A | 1/2000 | Tormala et al. |
| 6,019,762 A | 2/2000 | Cole |
| 6,022,352 A | 2/2000 | Vandewalle |
| 6,036,701 A | 3/2000 | Rosenman |
| 6,048,342 A | 4/2000 | Zucherman et al. |
| 6,068,648 A | 5/2000 | Cole et al. |
| 6,083,244 A | 7/2000 | Lubbers et al. |
| 6,102,914 A | 8/2000 | Bulstra et al. |
| 6,126,661 A | 10/2000 | Faccioli et al. |
| 6,126,663 A | 10/2000 | Hair |
| 6,146,384 A | 11/2000 | Lee et al. |
| 6,161,350 A | 12/2000 | Espinosa |
| 6,168,595 B1 | 1/2001 | Durham et al. |
| 6,183,472 B1 | 2/2001 | Lutz |
| 6,183,474 B1 | 2/2001 | Bramlet et al. |
| 6,248,108 B1 | 6/2001 | Tormala et al. |
| 6,251,111 B1 | 6/2001 | Barker et al. |
| 6,267,767 B1 | 7/2001 | Strobel et al. |
| 6,287,313 B1 | 9/2001 | Sasso |
| 6,306,136 B1 | 10/2001 | Baccelli |
| 6,319,254 B1 | 11/2001 | Giet et al. |
| 6,355,043 B1 | 3/2002 | Adam |
| 6,361,537 B1 | 3/2002 | Anderson |
| 6,361,538 B1 | 3/2002 | Fenaroli et al. |
| 6,371,989 B1 | 4/2002 | Chauvin et al. |
| 6,379,355 B1 | 4/2002 | Zucherman et al. |
| 6,379,363 B1 | 4/2002 | Herrington et al. |
| 6,409,767 B1 | 6/2002 | Perice et al. |
| 6,423,061 B1 | 7/2002 | Bryant |
| 6,423,067 B1 | 7/2002 | Eisermann |
| 6,440,169 B1 | 8/2002 | Elberg et al. |
| 6,458,134 B1 | 10/2002 | Songer et al. |
| 6,468,277 B1 | 10/2002 | Justin et al. |
| 6,468,309 B1 | 10/2002 | Lieberman |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,489,309 B1 | 12/2002 | Singh et al. |
| 6,491,714 B1 | 12/2002 | Bennett |
| 6,506,192 B1 | 1/2003 | Gertzman et al. |

(56) References Cited

U.S. PATENT DOCUMENTS

| | | |
|---|---|---|
| 6,511,481 B2 | 1/2003 | von Hoffmann et al. |
| 6,520,907 B1 | 2/2003 | Foley et al. |
| 6,527,774 B2 | 3/2003 | Lieberman |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,558,389 B2 | 5/2003 | Clark et al. |
| 6,562,046 B2 | 5/2003 | Sasso |
| 6,562,049 B1 | 5/2003 | Norlander et al. |
| 6,579,293 B1 | 6/2003 | Chandran |
| 6,582,453 B1 | 6/2003 | Tran et al. |
| 6,585,730 B1 | 7/2003 | Foerster |
| 6,585,740 B2 | 7/2003 | Schlapfer et al. |
| 6,589,249 B2 | 7/2003 | Sater et al. |
| 6,599,297 B1 | 7/2003 | Carlsson et al. |
| 6,610,091 B1 | 8/2003 | Reiley |
| 6,613,050 B1 | 9/2003 | Wagner et al. |
| 6,626,944 B1 | 9/2003 | Taylor |
| 6,632,224 B2 | 10/2003 | Cachia et al. |
| 6,648,890 B2 | 11/2003 | Culbert et al. |
| 6,648,893 B2 | 11/2003 | Dudasik |
| 6,669,698 B1 | 12/2003 | Tromanhauser et al. |
| 6,669,729 B2 | 12/2003 | Chin |
| 6,673,074 B2 | 1/2004 | Shluzas |
| 6,685,706 B2 | 2/2004 | Padget et al. |
| 6,733,534 B2 | 5/2004 | Sherman |
| 6,752,831 B2 | 6/2004 | Sybert et al. |
| 6,761,720 B1 | 7/2004 | Senegas |
| 6,770,075 B2 | 8/2004 | Howland |
| 6,793,656 B1 | 9/2004 | Mathews |
| 6,796,983 B1 | 9/2004 | Zucherman et al. |
| 6,808,526 B1 | 10/2004 | Magerl et al. |
| 6,835,205 B2 | 12/2004 | Atkinson et al. |
| 6,887,243 B2 | 5/2005 | Culbert |
| 6,890,333 B2 | 5/2005 | von Hoffmann et al. |
| 6,908,465 B2 | 6/2005 | von Hoffmann et al. |
| 6,921,403 B2 | 7/2005 | Cragg et al. |
| 6,923,811 B1 | 8/2005 | Carl et al. |
| 6,929,606 B2 | 8/2005 | Ritland |
| 6,942,668 B2 | 9/2005 | Padget et al. |
| 6,945,975 B2 | 9/2005 | Dalton |
| 6,951,561 B2 | 10/2005 | Warren et al. |
| 7,060,068 B2 | 6/2006 | Tromanhauser et al. |
| 7,070,601 B2 | 7/2006 | Culbert et al. |
| 7,074,203 B1 | 7/2006 | Johanson et al. |
| 7,326,211 B2 | 2/2008 | Padget et al. |
| 7,422,594 B2 | 9/2008 | Zander |
| 7,488,326 B2 | 2/2009 | Elliott |
| 7,556,629 B2 | 7/2009 | von Hoffmann et al. |
| 7,625,378 B2 | 12/2009 | Foley |
| 7,699,878 B2 | 4/2010 | Pavlov et al. |
| 7,846,183 B2 | 12/2010 | Blain |
| 8,109,977 B2 | 2/2012 | Culbert et al. |
| 2001/0027320 A1 | 10/2001 | Sasso |
| 2001/0049529 A1 | 12/2001 | Cachia et al. |
| 2001/0049530 A1 | 12/2001 | Culbert et al. |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |
| 2003/0028250 A1 | 2/2003 | Reiley et al. |
| 2003/0063582 A1 | 4/2003 | Mizell et al. |
| 2003/0065330 A1 | 4/2003 | Zucherman et al. |
| 2003/0069582 A1 | 4/2003 | Culbert |
| 2003/0097132 A1 | 5/2003 | Marty et al. |
| 2003/0220643 A1 | 11/2003 | Ferree |
| 2003/0229350 A1 | 12/2003 | Kay |
| 2004/0006391 A1 | 1/2004 | Reiley |
| 2004/0049190 A1 | 3/2004 | Biedermann et al. |
| 2004/0097941 A1 | 5/2004 | Weiner et al. |
| 2004/0127906 A1* | 7/2004 | Culbert .............. A61B 17/7064 606/247 |
| 2004/0143734 A1 | 7/2004 | Buer et al. |
| 2004/0186482 A1 | 9/2004 | Kolb et al. |
| 2004/0199162 A1 | 10/2004 | Von et al. |
| 2004/0225292 A1 | 11/2004 | Sasso et al. |
| 2004/0254575 A1 | 12/2004 | Obenchain et al. |
| 2005/0033434 A1 | 2/2005 | Berry |
| 2005/0090833 A1 | 4/2005 | Dipoto |
| 2005/0119657 A1 | 6/2005 | Goldsmith |
| 2005/0131411 A1 | 6/2005 | Culbert |
| 2005/0137595 A1 | 6/2005 | Hoffmann et al. |
| 2005/0143734 A1 | 6/2005 | Cachia et al. |
| 2005/0149030 A1 | 7/2005 | Serhan et al. |
| 2005/0216026 A1 | 9/2005 | Culbert |
| 2005/0251142 A1 | 11/2005 | Hoffmann et al. |
| 2005/0256525 A1 | 11/2005 | Culbert et al. |
| 2005/0283238 A1 | 12/2005 | Reiley |
| 2006/0015105 A1 | 1/2006 | Warren et al. |
| 2006/0030872 A1 | 2/2006 | Culbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0058790 A1 | 3/2006 | Carl et al. |
| 2006/0079908 A1 | 4/2006 | Lieberman |
| 2006/0084977 A1 | 4/2006 | Lieberman |
| 2006/0085010 A1 | 4/2006 | Lieberman |
| 2006/0100707 A1 | 5/2006 | Stinson et al. |
| 2006/0122609 A1 | 6/2006 | Mirkovic et al. |
| 2006/0122610 A1 | 6/2006 | Culbert et al. |
| 2006/0195103 A1 | 8/2006 | Padget et al. |
| 2006/0217711 A1 | 9/2006 | Stevens et al. |
| 2007/0016191 A1 | 1/2007 | Culbert et al. |
| 2007/0118132 A1 | 5/2007 | Culbert et al. |
| 2007/0123868 A1 | 5/2007 | Culbert et al. |
| 2008/0097436 A1 | 4/2008 | Culbert et al. |
| 2008/0108996 A1 | 5/2008 | Padget et al. |
| 2008/0287981 A1 | 11/2008 | Culbert et al. |
| 2008/0306537 A1 | 12/2008 | Culbert |
| 2009/0069813 A1 | 3/2009 | von Hoffmann et al. |
| 2009/0105745 A1 | 4/2009 | Culbert |
| 2009/0149857 A1 | 6/2009 | Culbert et al. |
| 2010/0331891 A1 | 12/2010 | Culbert et al. |
| 2011/0087296 A1 | 4/2011 | Reiley et al. |
| 2013/0245703 A1 | 9/2013 | Warren et al. |
| 2014/0257408 A1* | 9/2014 | Trieu ................. A61B 17/8875 606/301 |

FOREIGN PATENT DOCUMENTS

| | | |
|---|---|---|
| EP | 0525352 A1 | 2/1993 |
| EP | 0625336 A2 | 11/1994 |
| EP | 1046376 A1 | 10/2000 |
| EP | 0853929 B1 | 9/2002 |
| EP | 1374784 A1 | 1/2004 |
| EP | 1453413 A2 | 9/2004 |
| EP | 1757529 A1 | 2/2007 |
| FR | 2699065 | 6/1994 |
| FR | 2728778 A1 | 7/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| GB | 2157788 A | 10/1985 |
| GB | 2173565 A | 10/1986 |
| JP | 64-052439 A | 2/1989 |
| JP | 06-319742 A | 11/1994 |
| JP | 10-085232 A | 4/1998 |
| JP | 11-089854 A | 4/1999 |
| JP | 4309763 B2 | 8/2009 |
| WO | 91/09572 A1 | 7/1991 |
| WO | 99/62417 A1 | 12/1999 |
| WO | 00/67652 A2 | 11/2000 |
| WO | 01/80751 A1 | 11/2001 |
| WO | 03/43488 A2 | 5/2003 |
| WO | 2004/008949 A2 | 1/2004 |
| WO | 2004/064603 A2 | 8/2004 |
| WO | 2004/078220 A2 | 9/2004 |
| WO | 2004/078221 A2 | 9/2004 |

(56) References Cited

FOREIGN PATENT DOCUMENTS

| WO | 2004/098453 | A2 | 11/2004 |
| WO | 2006/017507 | A2 | 2/2006 |
| WO | 2006/063083 | A1 | 6/2006 |
| WO | 2006/108067 | A2 | 10/2006 |
| WO | 2007/124130 | A2 | 11/2007 |

OTHER PUBLICATIONS

May 23, 2003 International Search Report received in corresponding PCT App. No. PCT/US02/37102.
Mar. 31, 2010 Office Action for Japanese Patent Application No. 2005-505552 filed on Jul. 18, 2003.
Mar. 23, 2011 Office Action for Japanese Application No. 2005-505552 filed Jul. 18, 2003.
King, M.D., Don, "Internal Fixation for Lumbosacral Fusion", The Journal of Bone and Joint Surgery, J. Bone Joint Surg Am. 1948; 30: 560-578.
European Search Report for Application No. EP 02719402.
Aug. 4, 2009 Extended European Search Report received in European Application No. 09164698.4, 5 pages.
Apr. 22, 2004 International Search Report for App. No. PCT/US03/23645 filed Jul. 18, 2003.
Apr. 19, 2007 Office Action for European Application No. 02719402.6 filed Mar. 29, 2002.
Apr. 13, 2006 International Search Report for App. No. PCT/US2005/044321.
Bone fixation system, U.S. Appl. No. 09/558,057.

\* cited by examiner

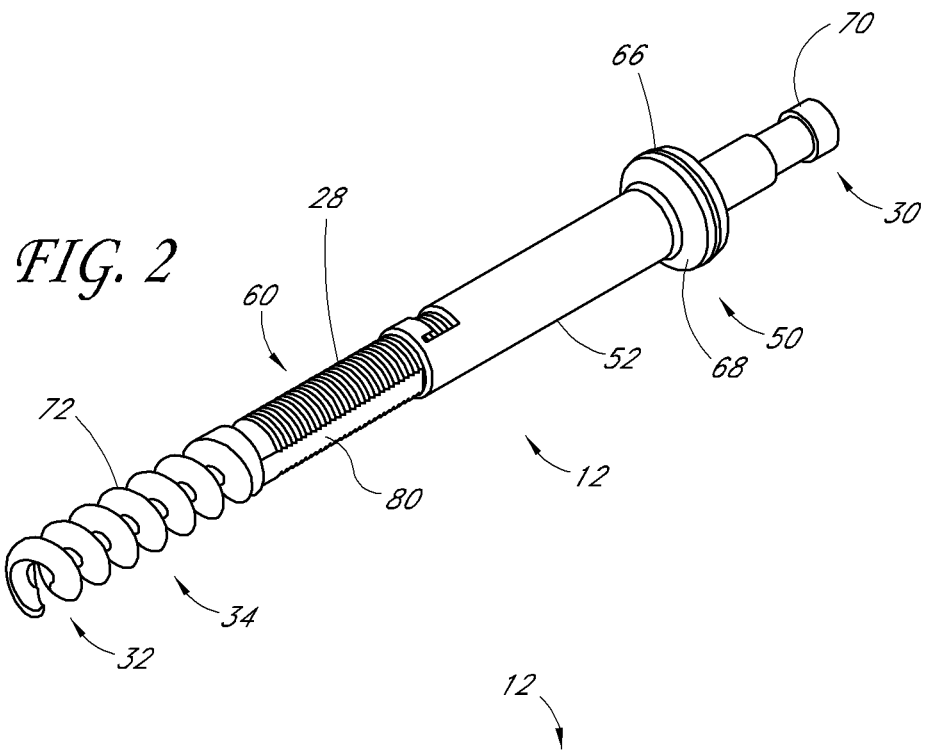
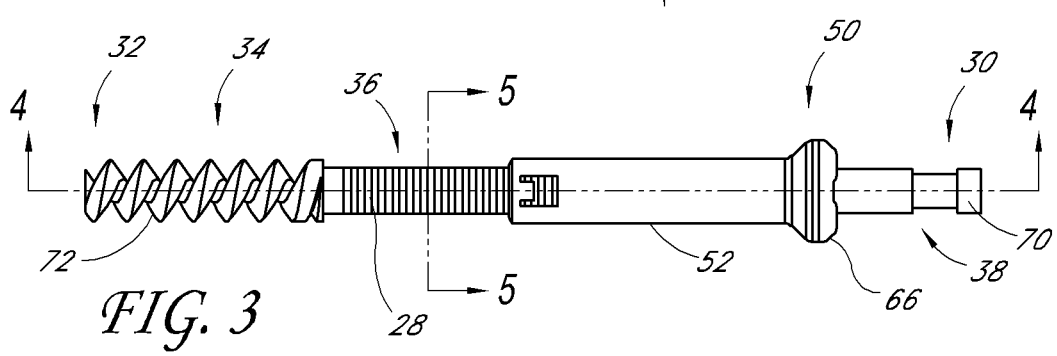
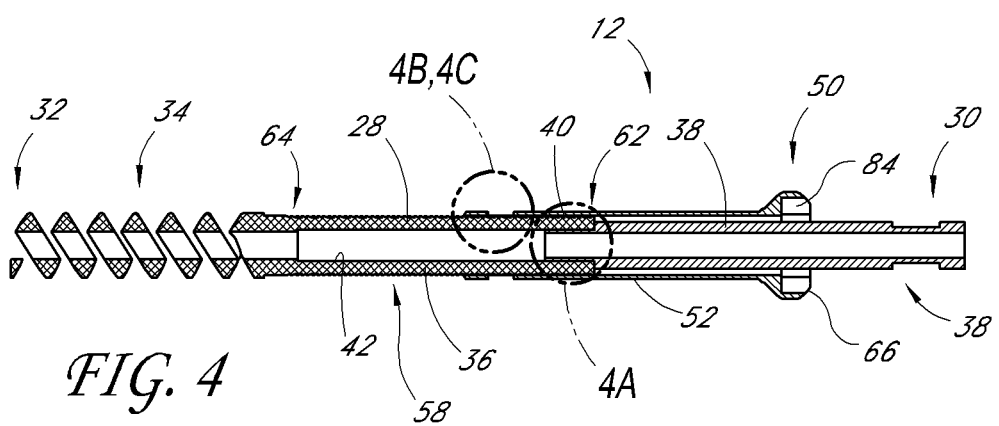

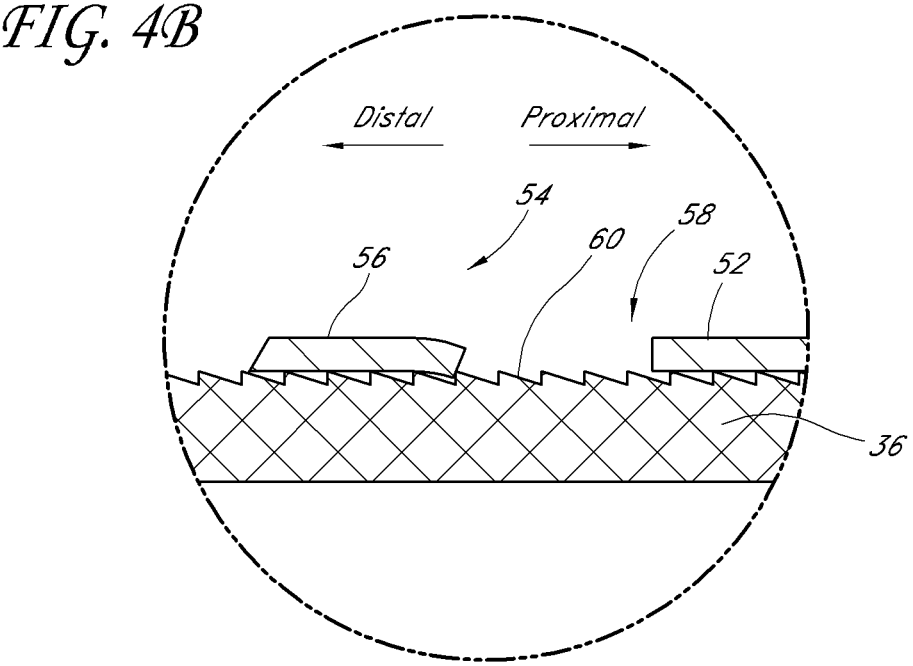
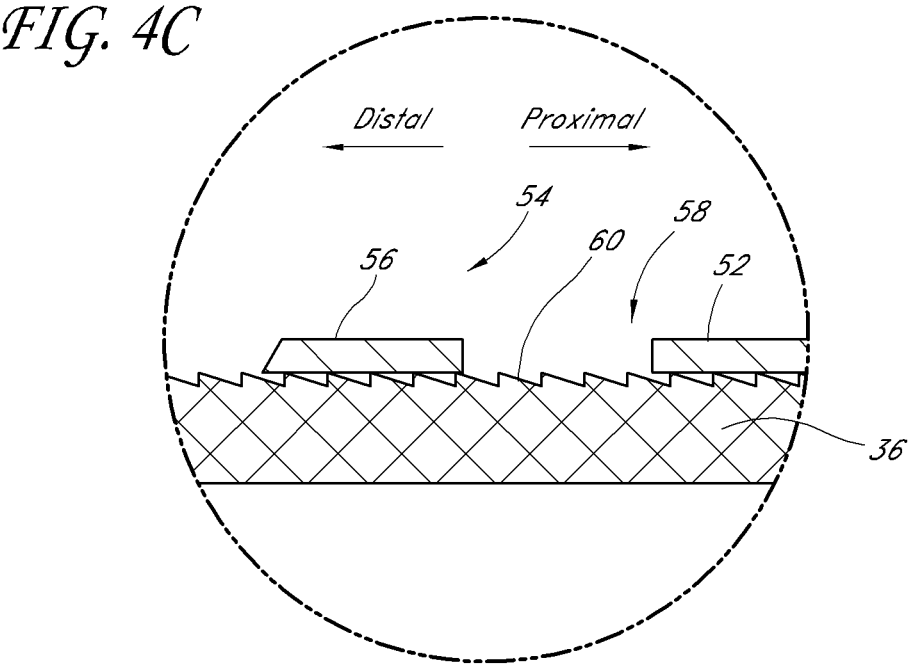

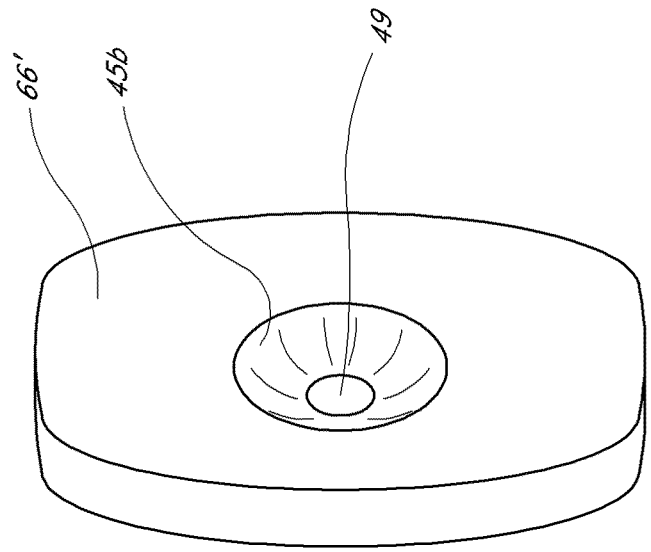
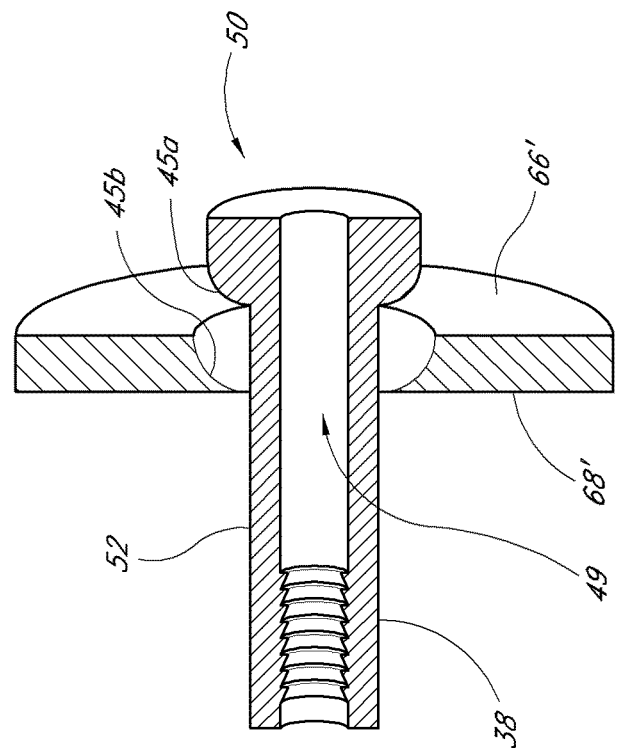
FIG. 8
FIG. 7

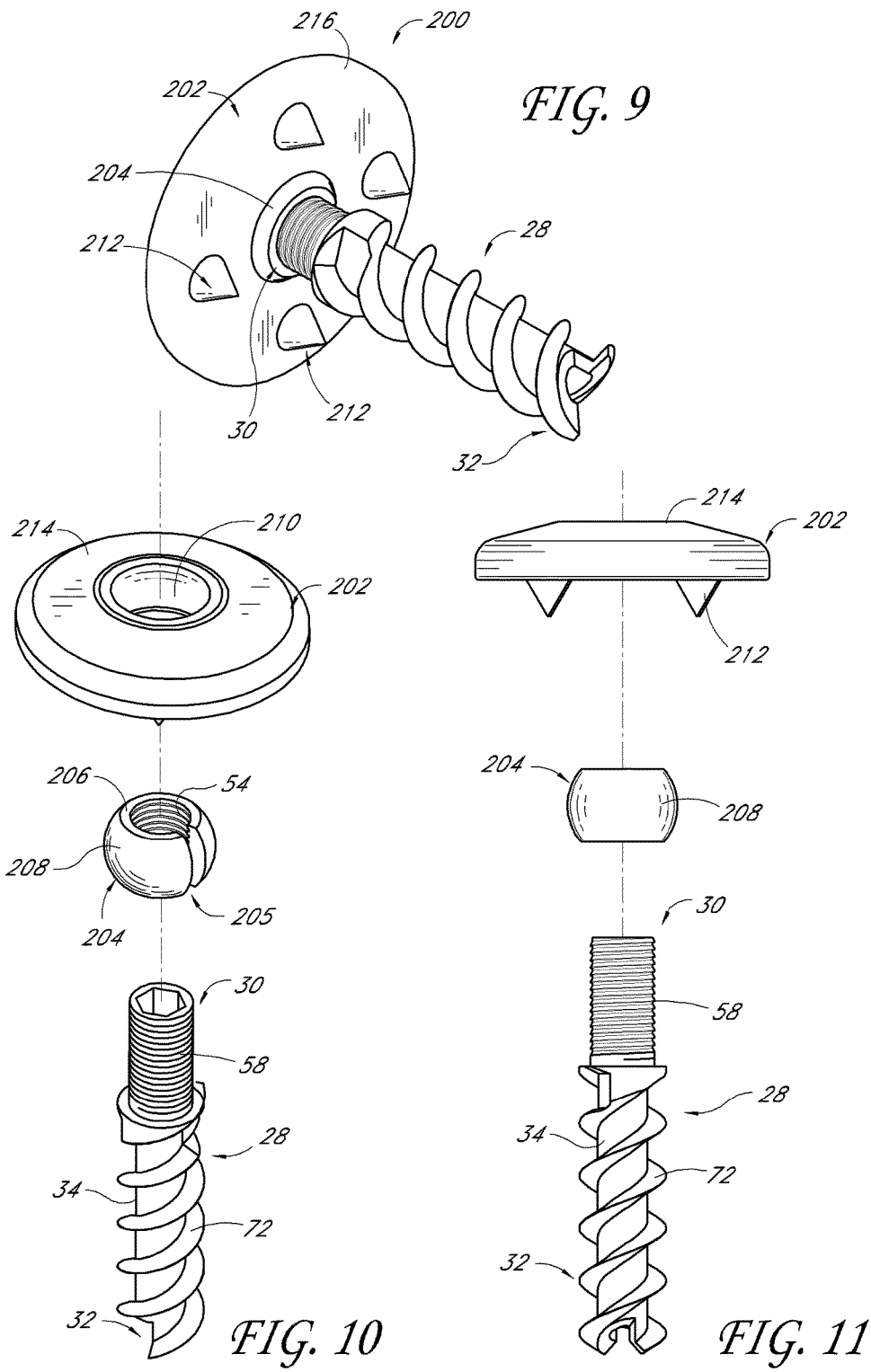

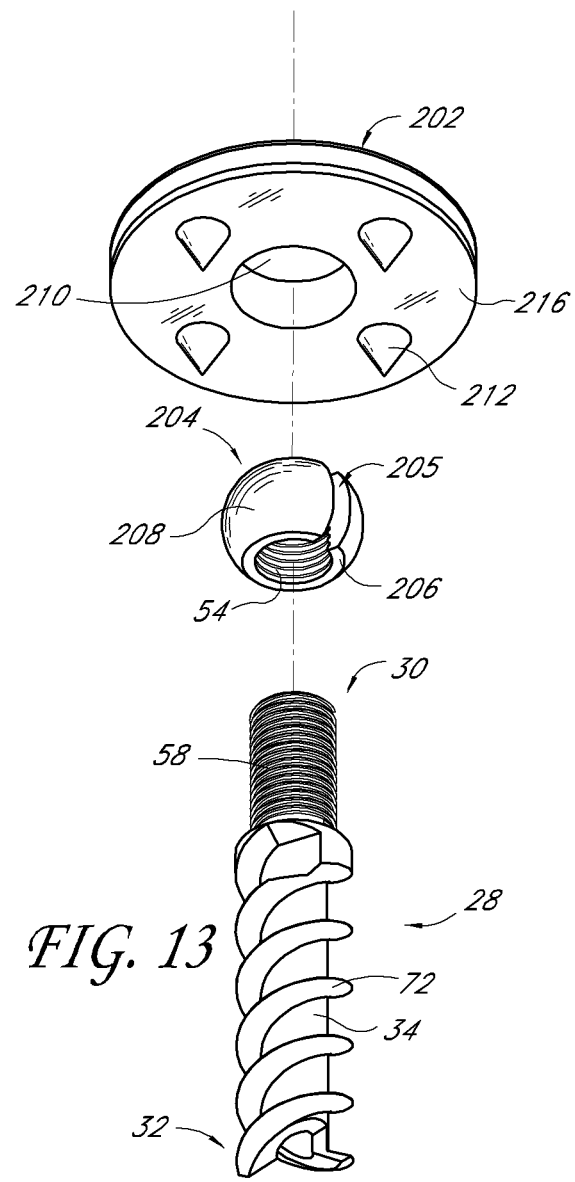
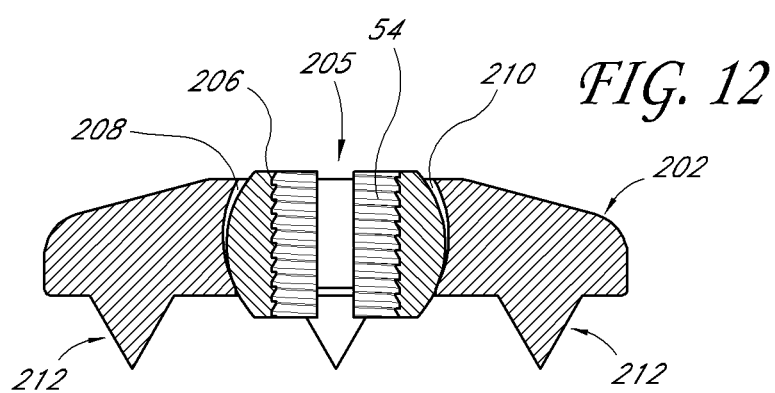

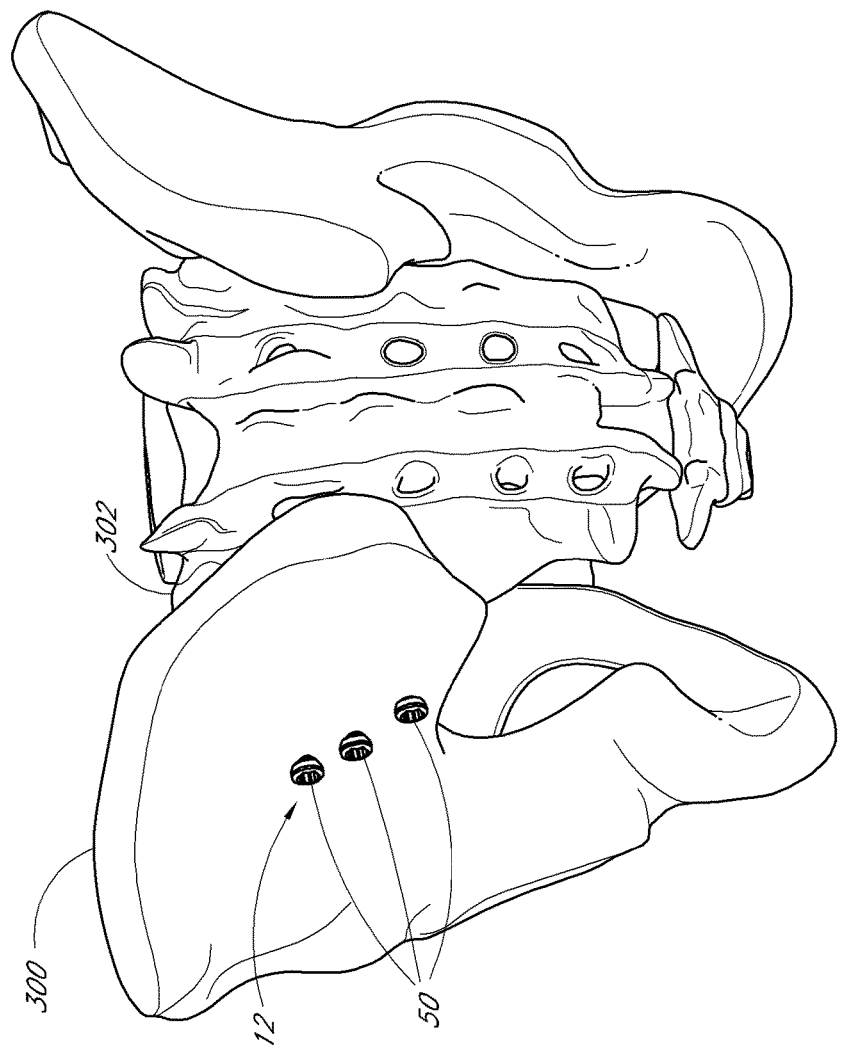

METHOD AND APPARATUS FOR SACROILIAC JOINT FIXATION

CROSS-REFERENCE TO RELATED APPLICATIONS

This application is a continuation of U.S. application Ser. No. 14/030,391, filed Sep. 18, 2013, which claims a priority benefit to U.S. Provisional Application No. 61/842,664, filed Jul. 3, 2013, the entire disclosure of each is hereby incorporated by reference in its entirety and should be considered a part of this specification

BACKGROUND

Field of the Invention

The present invention relates to medical devices and, more particularly, to methods and apparatus for sacroiliac joint stabilization.

Description of the Related Art

The sacroiliac joint is the joint between the sacrum and the ilium of the pelvis. Strong ligaments connect the sacrum to the ilium. The sacrum supports the spine and is supported on each side by an ilium. The sacroiliac joint is a synovial joint with cartilage and irregular elevations and depressions that produce interlocking of the two bones.

Pain in the sacroiliac joint can be caused by a number of conditions, including fracture or dislocation of the pelvis, degenerative arthritis, sacroiliitis (inflammation of the sacroiliac joint), or osteitis condensans ilii. One method for treatment of sacroiliac joint dysfunction is fusion of the sacroiliac joint. Fusion can be accomplished in a number of ways, for example an anterior approach, a posterior approach, or percutaneous screw fixation. The anterior approach can involve an incision along the iliac crest to the anterior superior iliac spine, followed by stripping the iliacus muscle to gain access to the sacroiliac joint. This approach poses a danger of damaging the L5 nerve root which is positioned near the sacroiliac joint. The posterior approach can use any of a number of different incisions, followed by stripping the gluteus maximus off the ilium to gain access to the joint. Both the anterior and posterior approaches pose risk of infection, and require relatively large incisions, resulting in unsightly scarring.

Percutaneous sacroiliac joint fusion can reduce the size of necessary incisions and lower the risk of infection through the minimally invasive introduction of joint fixation elements. Such methods typically include various fixation systems that are used for the stabilization of the sacroiliac joint. These fixation systems may include a variety of longitudinal elements such as screws which span the sacroiliac joint and are affixed to the sacrum through the ilium. These systems may be affixed to one side of the patient or to both sides.

Notwithstanding the variety of efforts in the prior art, there remains a need for a fixation device for sacroiliac joint stabilization with improved locking force, which resists migration and rotation, and which can be easily and rapidly deployed.

SUMMARY

There is provided in accordance with one aspect of the present invention, a bone fixation device. The device includes an elongate body, having a proximal end and a distal end; a distal anchor on the distal end; a retention structure on the body, proximal to the anchor; a proximal anchor, moveably carried by the body; at least one complementary retention structure on the proximal anchor configured to permit proximal movement of the body with respect to the proximal anchor but to resist distal movement of the body with respect the proximal anchor; and an inner member disposed within the elongate body, the inner member comprising a distal end configured to abut the distal anchor when proximally retracted.

In some embodiments, the distal anchor is configured to flare outwardly upon proximal movement of the inner member. In some embodiments, the distal end of the inner member is tapered. In some embodiments, the distal anchor comprises a helical flange having a plurality of slits formed therein. In some embodiments, the distal anchor is configured to be advanced through a bore in the ilium and into the sacrum. In some embodiments, the proximal anchor comprises a tubular housing. In some embodiments, the device further comprises a flange configured to receive the proximal anchor, the proximal anchor and the flange having complementary surface structures to permit angular adjustment with respect to the longitudinal axis of the proximal anchor and the body and the longitudinal axis of the flange. In some embodiments, the corresponding surfaces of the proximal anchor and the flange comprise a spherical outer surface of the proximal anchor and a corresponding spherical recess in the flange. In some embodiments, the elongate body has a length of between about 30 mm and about 120 mm. In some embodiments, the elongate body has a maximum diameter of between about 3 mm and about 12 mm. In some embodiments, the elongate body comprise an interior passageway in fluid communication with at least one exit hole. In some embodiments, the elongate body comprises a plurality of exit holes in fluid communication with the interior passageway.

According to another aspect, a method of providing bone fixation is disclosed. The method includes positioning a fixation device against the bone, the fixation device comprising a body having a distal anchor, a proximal anchor, and an inner member disposed within the body; advancing the distal anchor of the fixation device into the bone; axially shortening the fixation device by reducing the distance between the distal anchor and the proximal anchor, such that a locking element on the proximal anchor engages at least one retention structure on the body; and proximally retracting the inner member to cause the distal anchor to flare outwardly.

In some embodiments, axially shortening the fixation device comprises axially advancing the proximal anchor without rotating the proximal anchor with respect to the body. In some embodiments, the bone comprises an ilium, and wherein advancing the distal anchor comprises advancing the distal anchor through a bore in the ilium and into a sacrum. In some embodiments, proximally axially shortening the fixation device and proximally retracting the inner member apply compression between the sacrum and the ilium. In some embodiments, the method further comprises introducing bone graft material, bone growth promoters, and/or bone cement into the sacroiliac joint. In some embodiments, the body has a length of between about 30 mm and about 120 mm. In some embodiments, the body has a maximum diameter of between about 3 mm and about 12 mm. In some embodiments, the distal anchor comprises a helical flange having a plurality of slits formed therein.

In accordance with another aspect of the present invention, a sacroiliac joint fixation device is provided. The device includes an elongate body having a proximal end and a distal end, a distal anchor on the distal end, and a retention structure on the body, proximal to the anchor. A proximal anchor is movably carried by the body. At least one complementary retention structure is included on the proximal anchor, and is configured to permit proximal movement of the body with respect to the proximal anchor, but to resist distal movement of the body with respect to the proximal anchor. A flange is configured to receive the proximal anchor, the proximal anchor and flange having complementary surface structures to permit angular adjustment with respect to the longitudinal axis of the proximal anchor and the body, and the longitudinal axis of the flange.

In accordance with another aspect of the present invention, a method of providing sacroiliac joint fixation is disclosed. A fixation device that comprises a body having a distal anchor and a proximal anchor can be provided. The distal anchor can be advanced through an ilium of a pelvis and into a sacrum. The fixation device can then be rotated to engage the distal anchor with the sacrum. Next, the fixation device can be axially shortened by reducing the distance between the distal anchor and the proximal anchor, such that a locking element on the proximal anchor engages at least one retention structure on the body thereby applying compression between the sacrum and the ilium.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 2 is a side perspective view of an exemplary fixation device similar to that of FIG. 1.

FIG. 3 is a side elevational view of the fixation device of FIG. 2.

FIG. 4 is a cross-sectional view taken through line 4-4 of FIG. 3.

FIG. 4B is an enlarged view of portion 4B of FIG. 4 with the fixation device in a first position.

FIG. 4C is an enlarged view of portion 4C of FIG. 4 with the fixation device in a second position.

FIG. 7 is a cross sectional view through an angularly adjustable proximal anchor plate.

FIG. 8 is a front perspective view of the proximal anchor plate of FIG. 7.

FIG. 9 is a bottom perspective view of a modified embodiment of a bone fixation device.

FIG. 10 is an unassembled side perspective view of the bone fixation device of FIG. 9.

FIG. 11 is an unassembled side view of the bone fixation device of FIG. 9.

FIG. 12 is a cross-sectional view of the flange and proximal anchor of the bone fixation device of FIG. 11.

FIG. 13 is an unassembled bottom perspective view of the bone fixation device of FIG. 9.

FIGS. 16A-H are various views of the pelvis and sacrum with the fixation device of FIG. 2 implanted therein.

DETAILED DESCRIPTION

Although the fixation devices of the present invention will be disclosed primarily in the context of a sacroilial fixation procedure, the methods and structures disclosed herein are intended for application in any of a variety medical applications, as will be apparent to those of skill in the art in view of the disclosure herein. For example, the bone fixation device may be applicable to proximal fractures of the femur, for spinal fixation, and a wide variety of fractures and osteotomies, the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. See e.g., U.S. Pat. No. 6,511,481, which is hereby incorporated by reference herein. A wide variety of phalangeal and metatarsal osteotomies and fractures of the foot may also be stabilized using the bone fixation devices described herein. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. Fractures of the fibular and tibial malleoli, pilon fractures and other fractures of the bones of the leg may be fixated and stabilized with these bone fixation devices with or without the use of plates, both absorbable or non-absorbing types, and with alternate embodiments of the current invention The fixation devices may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The fixation devices may also be used to attach sutures to the bone, such as in any of a variety of tissue suspension procedures. The bone fixation device described herein may be used with or without plate(s) or washer(s), all of which can be either permanent, absorbable, or combinations.

Figure 1:
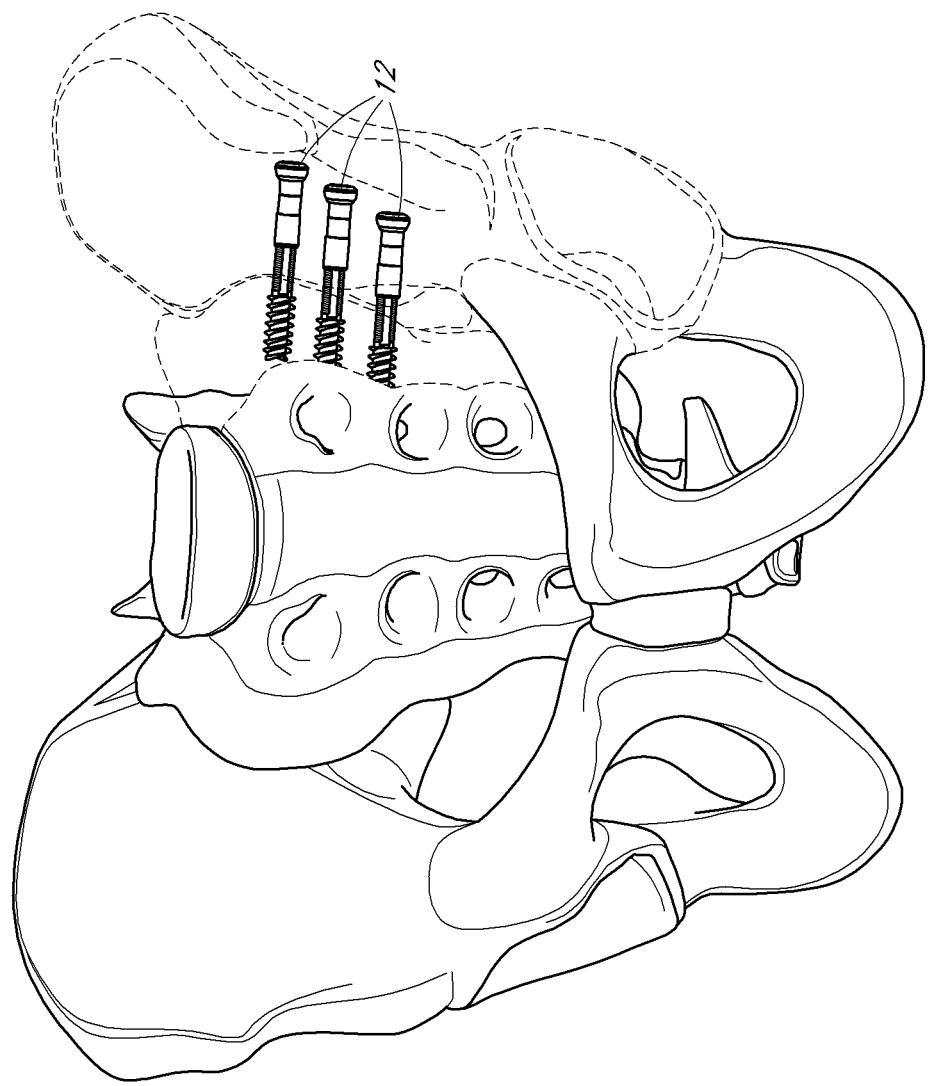
FIG. 1 is a front oblique view of a portion of a sacroiliac joint having a exemplary embodiment of a fixation device implanted therein.

Referring to FIG. 1, there is illustrated an exemplary embodiment of implanted bone fixation devices 12. The left ilium and a portion of the sacrum are shown as transparent in order to identify the locations of the fixation devices 12. In FIG. 1, three fixation devices 12 are positioned across the sacroiliac joint. As will be explained in more detail below, the bone fixation device 12 may be used in a variety of techniques to stabilize the sacroiliac joint. Accordingly, in modified embodiments, more than three or less than three fixation device can be used.

Referring to FIGS. 2-4, the exemplary fixation device 12 according to one embodiment will now be described in detail. The fixation device 12 comprises a body 28 that extends between a proximal end 30 and a distal end 32. The length, diameter and construction materials of the body 28 can be varied, depending upon the intended clinical application. In embodiments optimized for sacroiliac fixation in an adult human population, the body 28 will generally be within the range of from about 30-120 mm in length and within the range of from about 3-12 mm in maximum diameter. The length of the helical anchor, discussed below, may be about 8-100 millimeters. Of course, it is understood that these dimensions are illustrative and that they may be varied as required for a particular patient or procedure.

In one embodiment, the body 28 comprises titanium. However, as will be described in more detail below, other metals or bioabsorbable or nonabsorbable polymeric materials may be utilized, depending upon the dimensions and desired structural integrity of the finished fixation device 12.

The distal end 32 of the body 28 is provided with a cancellous bone anchor or distal cortical bone anchor 34. Generally for sacroilial fixation, the distal bone anchor 34 is adapted to be rotationally inserted into a portion of the sacrum. In the illustrated embodiment, the distal anchor 34 comprises a helical locking structure 72 for engaging cancellous and/or distal cortical bone. In the illustrated embodiment, the locking structure 72 comprises a flange that is wrapped around an axial lumen. The flange extends through at least one and generally from about 2 to about 50 or more full revolutions depending upon the axial length of the distal anchor and intended application. The flange will can complete from about 2 to about 20 revolutions. The helical flange 72 is provided with a pitch and an axial spacing to optimize the retention force within cancellous bone, to optimize compression.

The helical flange 72 of the illustrated embodiment has a generally triangular cross-sectional shape (see FIG. 4). However, it should be appreciated that the helical flange 72 can have any of a variety of cross sectional shapes, such as rectangular, oval or other as deemed desirable for a particular application through routine experimentation in view of the disclosure herein. The outer edge of the helical flange 72 defines an outer boundary. The ratio of the diameter of the outer boundary to the diameter of the central lumen can be optimized with respect to the desired retention force within the cancellous bone and giving due consideration to the structural integrity and strength of the distal anchor 34. Another aspect of the distal anchor 34 that can be optimized is the shape of the outer boundary and the central core, which in the illustrated embodiment are generally cylindrical.

The distal end 32 and/or the outer edges of the helical flange 72 may be atraumatic (e.g., blunt or soft). This inhibits the tendency of the fixation device 12 to migrate anatomically distally after implantation. Distal migration is also inhibited by the dimensions and presence of a proximal anchor 50, which will be described below.

A variety of other arrangements for the distal anchor 32 can also be used. For example, the various distal anchors described in co-pending U.S. patent application Ser. No. 10/012,687, filed Nov. 13, 2001 can be incorporated into the fixation device 12 described herein. The entire contents of this application is hereby expressly incorporated by reference. In particular, the distal anchor may comprise a single helical thread surrounding a central core, much as in a conventional screw, which has been cannulated to facilitate placement over a wire. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal bone, and whether the distal anchor is intended to engage exclusively cancellous bone or will also engage cortical bone.

Figure 4A:
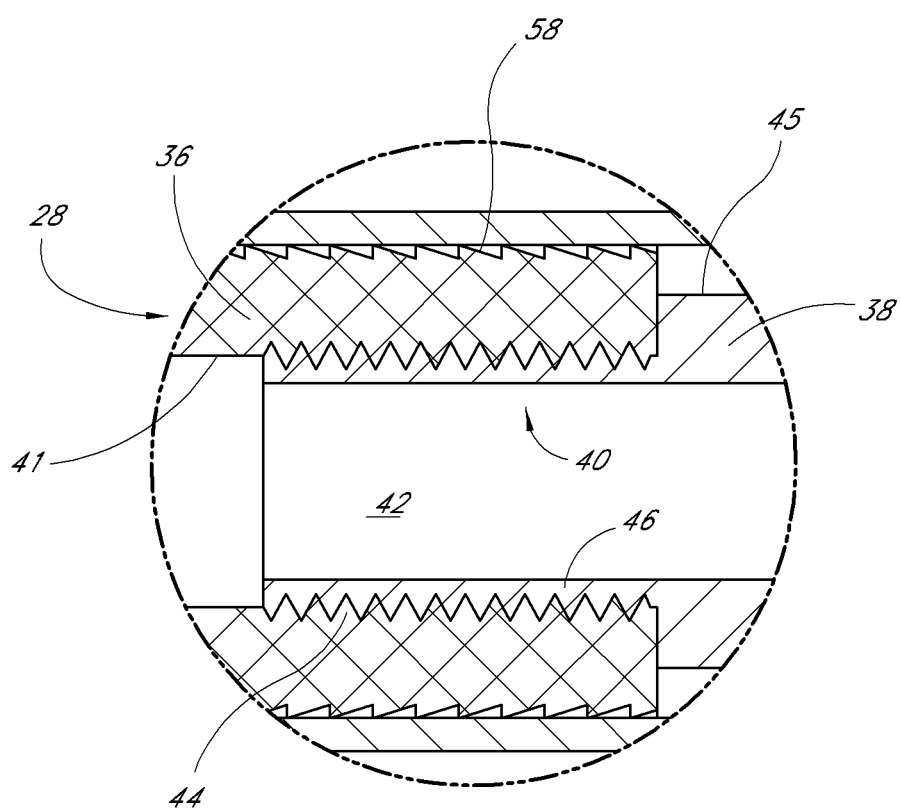
FIG. 4A is an enlarged view of portion 4A of FIG. 4.

With particular reference to FIGS. 3, 4, and 4A, the body 28 comprises a first portion 36 and a second portion 38 that are coupled together at a junction 40. In the illustrated embodiment, the first portion 36 carries the distal anchor 34 while the second portion 38 forms the proximal end 30 of the body 28. As will be explained in more detail below, in certain embodiments, the second portion 38 may be used to pull the body 28 and therefore will sometimes be referred to as a "pull-pin". The first and second portions 36, 38 are preferably detachably coupled to each other at the junction 40. In the illustrated embodiment, the first and second portions 36, 38 are detachably coupled to each other via interlocking threads. Specifically, as best seen in FIG. 4A, the body 28 includes an inner surface 41, which defines a central lumen 42 that preferably extends from the proximal end 30 to the distal end 32 throughout the body 28. At the proximal end of the first portion 36, the inner surface 41 includes a first threaded portion 44. The first threaded portion 44 is configured to mate with a second threaded portion 46, which is located on the outer surface 45 of the second portion 38. The interlocking annular threads of the first and second threaded portions 44, 46 allow the first and second portions 36, 38 to be detachably coupled to each other. In one modified embodiment, the orientation of the first and second threaded portions 44, 46 can be reversed. That is, the first threaded portion 44 can be located on the outer surface of the first portion 36 and the second threaded portion 46 can be located on the inner surface 41 at the distal end of the second portion 38. Any of a variety of other releasable complementary engagement structures may also be used, to allow removal of second portion 38 following implantation, as is discussed below.

In a modified arrangement, the second portion 38 can comprise any of a variety of tensioning elements for permitting proximal tension to be placed on the distal anchor 34 while the proximal anchor is advanced distally to compress the fracture. For example, any of a variety of tubes or wires can be removably attached to the first portion 36 and extend proximally to the proximal handpiece. In one such arrangement, the first portion 36 can include a releasable connector in the form of a latching element, such as an eye or hook. The second portion 38 can include a complementary releasable connector (e.g., a complementary hook) for engaging the first portion 36. In this manner, the second portion 38 can be detachably coupled to the first portion 36 such proximal traction can be applied to the first portion 36 through the second portion as will be explained below. Alternatively, the second portion 48 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein. It should also be appreciated that the body may be from a single piece as described in U.S. Pat. No. 6,511,481, which has been incorporated by reference herein.

As shown in FIG. 4, the body 28 is cannulated to accommodate installation over a placement wire as is understood in the art. The cross section of the illustrated central cannulation is circular but in other embodiments may be non circular, e.g., hexagonal, to accommodate a corresponding male tool for installation or removal of the second portion 38 of the body 28 as explained above. In other embodiments, the body 28 may partially or wholly solid.

With continued reference to FIGS. 2-4, the proximal end 30 of the body 28 may be provided with a rotational coupling 70, for allowing the second portion 38 of the body 28 to be rotationally coupled to a rotation device. The proximal end 30 of the body 28 may be desirably rotated to accomplish one or two discrete functions. In one application, the proximal end 30 is rotated to remove the second portion 38 of the body 28 following tensioning of the device to anchor an attachment to the bone. Rotation of the rotational coupling 70 may also be utilized to rotationally drive the distal anchor into the bone. Any of a variety of rotation devices may be utilized, such as electric drills or hand tools, which allow the clinician to manually rotate the proximal end 30 of the body. Thus, the rotational coupling 70 may have any of a variety of cross sectional configurations, such as one or more flats or splines.

In one embodiment, the rotational coupling 70 comprises a proximal projection of the body 28 having an axial recess with a polygonal cross section, such as a hexagonal cross section. The rotational coupling 70 is illustrated as a female component, machined or milled or attached to the proximal end 30 of the body 28. However, the rotational coupling may also be in the form of a male element, such as a hexagonal or other noncircular cross sectioned projection.

The proximal end 30 of the fixation device is provided with a proximal anchor 50. Proximal anchor 50 is axially distally moveable along the body 28, to permit compression of between the distal and proximal ends 32, 30 of the fixation device 12. As will be explained below, complementary locking structures such as threads or ratchet like structures between the proximal anchor 50 and the body 28 resist proximal movement of the anchor 50 with respect to the body 28 under normal use conditions. The proximal anchor 50 preferably can be axially advanced along the body 28 with and/or without rotation as will be apparent from the disclosure herein.

Referring to FIG. 4, the proximal anchor 50 comprises a housing 52 such as a tubular body, for coaxial movement along the body 28. As will be explained in more detail below, in certain embodiments, the housing 50 may have diameter sized to fit through an opening formed in fixation bar or plate.

In a final position, the distal end of the housing 52 preferably extends distally past the junction 40 between the first portion 36 and the second portion 38. The housing 52 is provided with one or more surface structures 54 such as a radially inwardly projecting flange 56 (see FIGS. 4B and 4C), for cooperating with complementary surface structures 58 on the first portion 36 of the body 28. In the illustrated embodiment, the complementary surface structures 58 comprise a series of annular ridges or grooves and/or threads 60. The surface structures 54 and complementary surface structures 58 permit distal axial travel of the proximal anchor 50 with respect to the body 28, but resist proximal travel of the proximal anchor 50 with respect to the body 28.

For example, as best seen in FIG. 4B, the proximal end of the flange 56 is biased towards the longitudinal axis of the body 28. As such, when the proximal anchor 50 is urged proximally with respect to the body 28, the flange 56 engages the grooves or ridges 60 of the complementary surface structures 58. This prevents proximal movement of the proximal anchor 50 with respect to the body 28. In contrast, as best seen in FIG. 4C, when the proximal anchor 50 is moved distally with respect to the body 28, the flange 56 can bend outwardly away from the body 28 and the ridges 60 so as to allow the proximal anchor 50 to move distally. Of course, those of skill in the art will recognize that there are a variety of other complementary surface structures, which permit one way ratchet like movement. For example, a plurality of annular rings or helical threads, ramped ratchet structures and the like for cooperating with an opposing ramped structure or pawl can also be used. In one embodiment, opposing screw threads are dimensioned to function as a ratchet. In other embodiments, the complementary surface structures can comprise complementary threads.

Retention structures 58 (e.g., grooves or threads) are spaced axially apart along the body 28, between a proximal limit 62 and a distal limit 64. The axial distance between proximal limit 62 and distal limit 64 is related to the desired axial working range of the proximal anchor 50, and thus the range of functional sizes of the fixation device 12. Thus, the fixation device 12 of the exemplary embodiment can provide compression between the distal anchor 34 and the proximal anchor 50 throughout a range of motion following the placement of the distal anchor in bone. That is, the distal anchor may be positioned within the cancellous and/or distal cortical bone of the sacrum, and the proximal anchor may be distally advanced with respect to the distal anchor throughout a range to provide compression without needing to relocate the distal anchor and without needing to initially locate the distal anchor in a precise position with respect to the proximal side of the ilium. Providing a working range throughout which tensioning of the proximal anchor is independent from setting the distal anchor allows a single device to be useful for a wide variety of fixation procedures, as well as eliminates the need for accurate device measurement. In addition, this arrangement allows the clinician to adjust the compression force during the procedure without adjusting the position of the distal anchor. In this manner, the clinician may focus on positioning the distal anchor sufficiently within the sacrum to avoid or reduce the potential for distal migration, which may damage the particularly delicate tissue, blood vessels, and/or nerves.

In many applications, the working range is at least about 10% of the overall length of the device, and may be as much as 20% or 50% or more of the overall device length. In the context of a sacroilial application, working ranges of up to about 15 mm or more may be provided, since estimates within that range can normally be readily accomplished within the clinical setting. The embodiments disclosed herein can be scaled to have a greater or a lesser working range, as will be apparent to those of skill in the art in view of the disclosure herein.

With reference back to FIGS. 2-4, the proximal anchor 50 includes a flange 66 that, as will be explained below, may be configured to sit against the outer surface of the ilium and/or a fixation rod or plate. The flange 66 is preferably an annular flange, to optimize the footprint or contact surface area between the flange 66 and the bone or fixation rod or plate. Circular or polygonal shaped flanges for use in sacroilial fixation will generally have a diameter of at least about 3 mm greater than the adjacent body 28 and often within the range of from about 2 mm to about 30 mm or more greater than the adjacent body 28.

Figure 5:
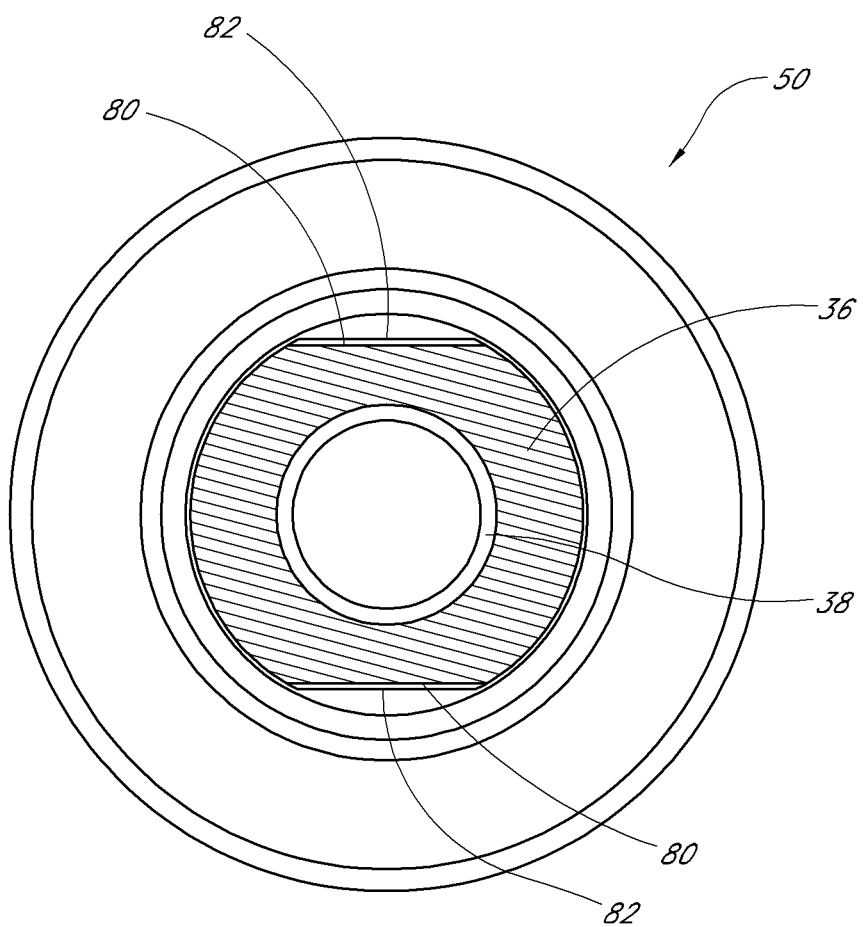
FIG. 5 is a cross-sectional view taken through line 5-5 of FIG. 3.

With particular reference to FIGS. 2 and 5, the fixation device may include an antirotation lock between the first portion 36 of the body 28 and the proximal collar 50. In the illustrated embodiment, the first portion 36 includes a pair of flat sides 80, which interact with corresponding flat structures 82 in the proximal collar 50. One or three or more axially extending flats may also be used. As such, rotation of the proximal collar 50 is transmitted to the first portion 36 and distal anchor 34 of the body 28. Of course, those of skill in the art will recognize various other types of splines or other interfit structures can be used to prevent relative rotation of the proximal anchor and the first portion 36 of the body 28.

To rotate the proximal collar, the flange 66 is preferably provided with a gripping structure to permit an insertion tool to rotate the flange 66. Any of a variety of gripping structures may be provided, such as one or more slots, flats, bores or the like. In one embodiment, the flange 44 is provided with a polygonal, and, in particular, a pentagonal or hexagonal recess 84 (see FIG. 4).

In a modified embodiment, the housing 52 of the proximal anchor 50 can include one or more one or more barbs that extend radially outwardly from the tubular housing 52. Such barbs provide for self tightening after the device has been implanted in the patient as described in a co-pending U.S. patent application Ser. No. 10/012,687, filed Nov. 13, 2001, which was incorporated by reference above. The barbs may be radially symmetrically distributed about the longitudinal axis of the housing 52. Each barb is provided with a transverse engagement surface, for anchoring the proximal anchor 50 in the bone. The transverse engagement surface may lie on a plane which is transverse to the longitudinal axis of the housing 50 or may be inclined with respect to the longitudinal axis of the tubular 50. In either arrangement, the transverse engagement surface 43 generally faces the contacting surface 68 of the flange 44. As such, the transverse engagement surface inhibits proximal movement of the proximal anchor with respect to the bone.

Figure 6A:
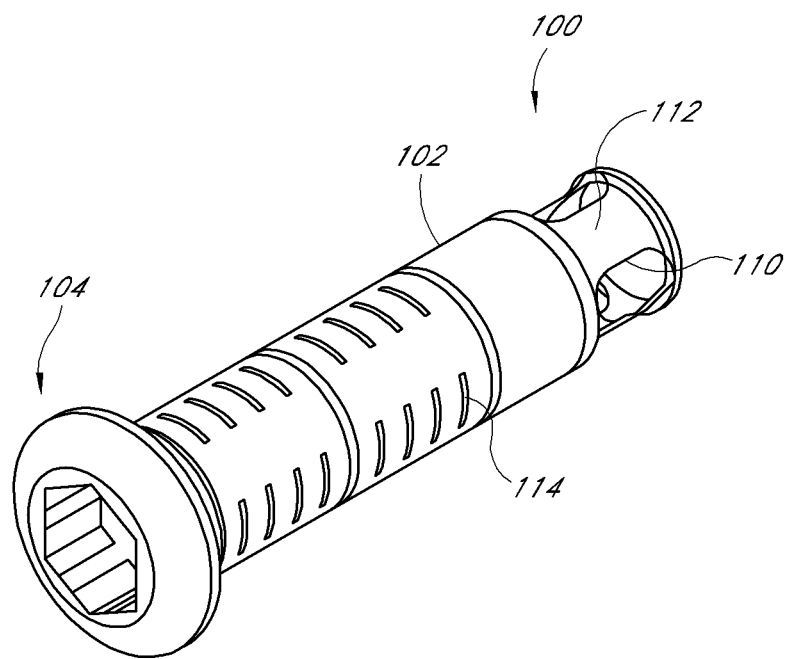
FIG. 6A is a side perspective view of another embodiment of a proximal anchor for the bone fixation device of FIG. 2.
Figure 6B:
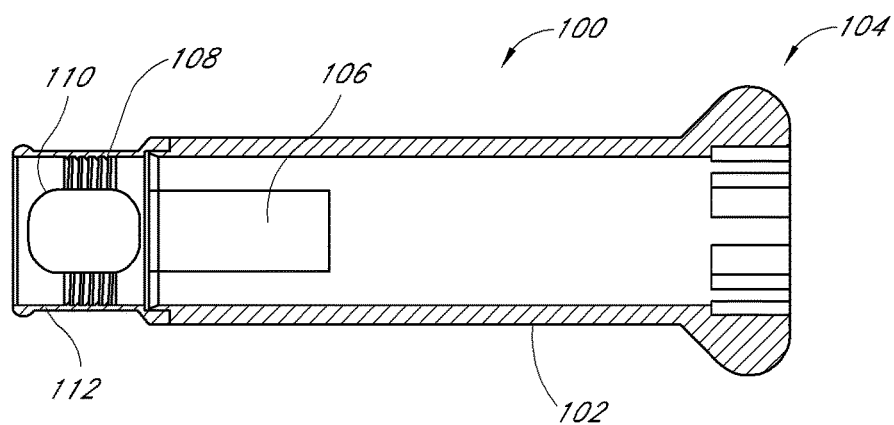
FIG. 6B is a cross-sectional view of the proximal anchor of FIG. 6A.

FIGS. 6A and 6B illustrate another embodiment of a proximal anchor 100. This embodiment also includes a tubular housing 102 and a flange 104 that may be configured as describe above with respect to FIGS. 2-4. The tubular housing 102 may include an anti-rotational lock, which, in the illustrated embodiment, is in the form of one or more sides 106 that interact with corresponding flat structures formed in the body 28 as described above.

In this embodiment, the surfaces structures comprises one or more teeth or grooves 112, which are configured to engage the complementary surfaces structures on the body 28 (see FIG. 2). One or more slots or openings 110 are formed in the tubular housing 102 to form one or more bridges 112, which carry the teeth 102. The anchor proximal anchor 100 may be pushed towards the distal end of the body and the teeth 102 can slide along the and over the complementary surface structures 58 on the body 28. In the illustrated embodiment, the bridge 113 may flex slightly away from the body 28 to allow such movement. The number and shape of the openings 110 and bridges 112 may be varied depending of the desired flexing of the bridges 112 when the proximal anchor 110 is moved distally over the body and the desired retention force of the distal anchor when appropriately tensioned. In one embodiment, the teeth on the proximal anchor 100 and the grooves on the body 28 may be configured such that the proximal anchor 100 can be rotated or threaded onto the pin in the distal direct and/or so that that the proximal anchor can be removed by rotation. The illustrated embodiment also advantageously includes visual indicia 114 (e.g., marks, grooves, ridges etc.) on the tubular housing 102 for indicating the depth of the proximal housing 100 within the bone.

Figure 6C:
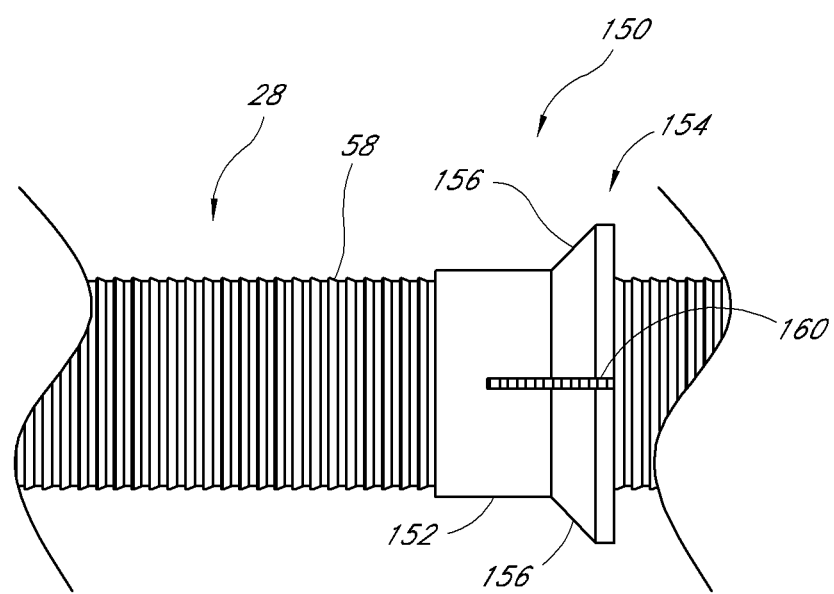
FIG. 6C is a side perspective view of another embodiment of a proximal anchor for the bone fixation device of FIG. 2.
Figure 6D:
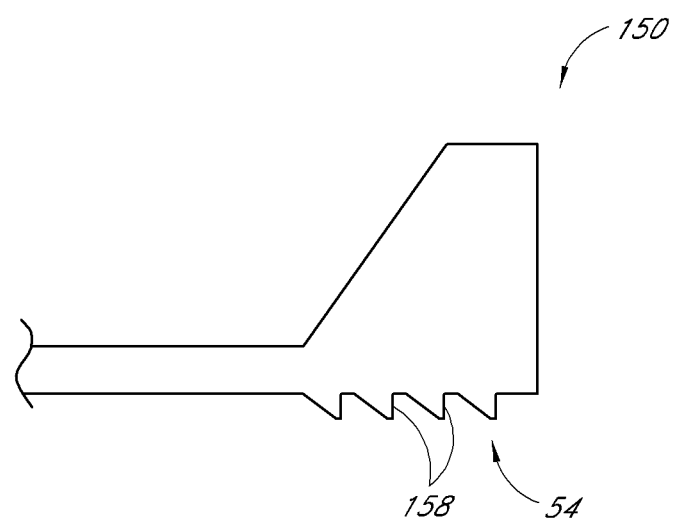
FIG. 6D is a cross-sectional view of the proximal anchor of FIG. 6C.

FIGS. 6C and 6D illustrate another embodiment of a proximal anchor 150. In this embodiment, the proximal anchor 150 comprises a housing 152 such as a tubular body, for coaxial movement along the body 28. The proximal anchor 150 also includes a flange 154 that is configured that to set against the outer surface of, for example, a bone or fixation bar or rod. In the illustrated embodiment, the flange 154 defines a contacting surface 156, which preferably forms an obtuse angle with respect to the exterior of the housing 152. However, in modified embodiments, the contacting surface 154 may be perpendicular or form an acute angle with respect to the housing 152.

Referring to FIG. 6D, in the illustrated embodiment, the complementary retention structures 54 comprise one or more inwardly projecting teeth or flanges 158, for cooperating with the complementary rentention structures 58 on the body 28. The complementary retention structures 58 of the body preferably comprise a plurality of annular ridges or grooves a first surface and a second surface. The first surface generally faces the proximal direction and is preferably inclined with respect to the longitudinal axis of the body 28. In contrast, the second surface generally faces the distal direction and lies generally perpendicular to the longitudinal axis of the body 28.

The proximal anchor 150 preferably includes one or more of axial slots 160. The axial slots 160 cooperate to form lever arm(s) on which the teeth or projections 158 are positioned. Thus, as the anchor 150 is pushed towards the distal end of the body 28, the teeth 158 can slide along the first surface and ride over the retention structures 58 of the body 28 as the teeth 158 are flexed away from the body 28.

After appropriate tensioning of the proximal anchor 150, the bone may push on the angled portion contacting surface 156 of the proximal anchor 150. This force is transmitted to the teeth 158 through the lever arms. As such, the teeth 158 are prevented from flexing away from the body 28, which keeps the teeth 158 engaged with the retention structures 58 of the body 28. By increasing the tensioning force, proximal movement of the proximal anchor 150 with respect to the body 28 is resisted.

The axial length and width of the slots 160 may be varied, depending upon the desired flexing of the lever arms when the proximal anchor 150 is moved distally over the body 28 and the desired retention force of the distal anchor when appropriately tensioned. For a relatively rigid material such as titanium, axial lengths and widths of the slots 160 are approximately 0.5 mm for a proximal anchor having a length of approximately 4 mm, an inner diameter of approximately 3 mm. As such, in the illustrated embodiment, the slots 160 extend through the flange 154 and at least partially into the housing 152.

In this embodiment, the proximal anchor 150 includes four teeth or flanges 158, which are positioned near the proximal end of the anchor 150. In modified embodiments, the proximal anchor 150 may include more or less teeth and/or the teeth may be positioned more distally or proximally on the anchor 150. It should also be appreciated that these retention structures may be configured such that the proximal anchor 150 may be proximally and/or distally advanced with rotation by providing for a screw like configuration between the retention structures.

Figure 6E:
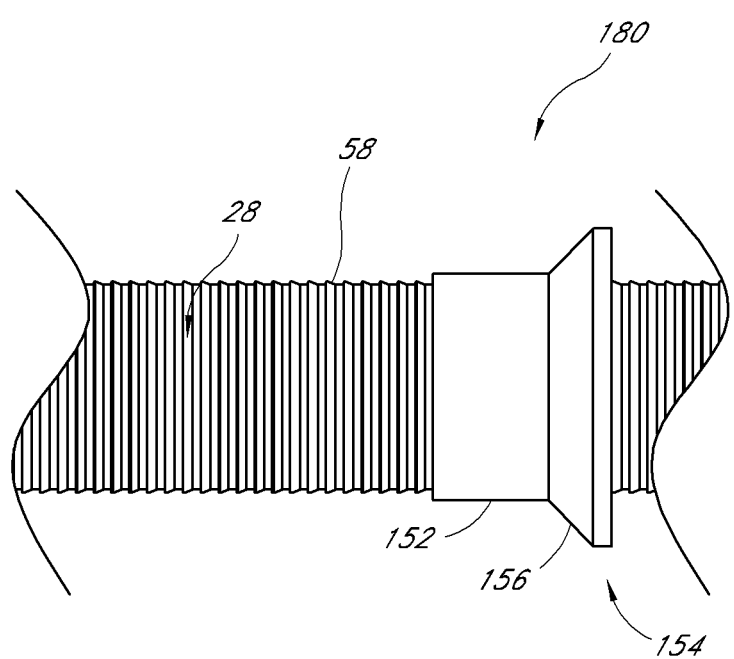
FIG. 6E is a cross-sectional view of another embodiment of a proximal anchor for the bone fixation device of FIG. 2.
Figure 6F:
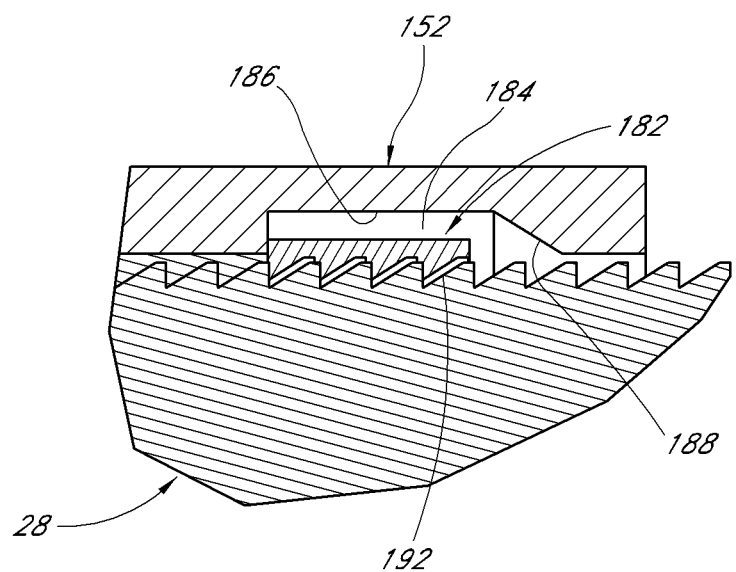
FIG. 6F is a cross-sectional view of the proximal anchor of FIG. 6E.

Another embodiment of a proximal anchor 180 is illustrated in FIGS. 6E and 6F. As with the previous embodiment, the proximal anchor 180 may include a tubular housing 152 and a flange 154 with a bone contacting surface 156. In this embodiment, the complementary structure of the proximal anchor 180 comprises an annular ring 182, which is positioned within an annular recess 184 that is preferably positioned at the distal end of the tubular housing 152. The annular recess 184 includes a proximal portion 186 and a distal portion 188.

The proximal portion 186 is sized and dimensioned such that as the proximal anchor 180 is advanced distally over the body 28 the annular ring 182 can ride over the complementary retention structures 58 of the body 28. That is, the proximal portion 182 provides a space for the annular ring 182 can move radially away from the body 28 as the proximal anchor 180 is advanced distally. Preferably, the annular ring 182 is made from a material that provides sufficient strength and elasticity such as, for example, stainless steel or titanium. The annular ring 182 is preferably split such that it can be positioned over the body 405. In the illustrated embodiment, the annular ring 182 includes a plurality of teeth 192 although in modified embodiments the annular ring 182 may be formed without the teeth.

The distal portion 188 of the recess 184 is sized and dimensioned such that after the proximal anchor 180 is appropriately tensioned the annular ring 192 becomes wedged between the body 28 and an angled engagement surface of the distal portion 188. In this manner, proximal movement of the proximal anchor 180 with respect to the body is prevented. Although not illustrated, it should be appreciated that in modified embodiments, the ring 192 can be formed without a gap. Other embodiments and further details of the proximal anchor described above can be found in U.S. patent application Ser. No. 09/990,587, filed Nov. 19, 2001, which is hereby incorporated by reference herein.

With reference back to FIGS. 2-4, in the illustrated embodiment, the contacting surface 68 of the flange 44 is tapered and generally faces the outer surface of the ilium, fixation rod, and/or plate. In other embodiments, the bone contacting surface 69 can reside in or approximately on a plane, which is perpendicular with respect to the longitudinal axis of the body 28. In other embodiments, other angular relationships between the bone contacting surface 68 of the flange 66 and the longitudinal axis of the body 28 and housing 52 may be utilized, depending upon the anticipated entrance angle of the body 28 and associated entrance point surface of the ilium.

The clinician may be provided an array of proximal anchors 50 of varying angular relationships between the contacting surface 68 and the longitudinal axis of the body 28 and housing 52 (e.g., 90°, 100°, 110°, 120°, and 130°). A single body 28 can be associated with the array such as in a single sterile package. The clinician upon identifying the entrance angle of the body 28 and the associated entrance point surface orientation can choose the anchor 50 from the array with the best fit angular relationship, for use with the body 28.

In accordance with a modified arrangement, illustrated in FIGS. 7 and 8, the proximal anchor 50 may be used with a washer 66' that is angularly adjustable with respect to the longitudinal axis of the body 28. More specifically, in this embodiment, the proximal anchor 50 and the washer 66' include corresponding semi-spherical or radiused surfaces 45a and 45b. The surface 45b surrounds an aperture 49 in the washer 66. This arrangement allows the proximal anchor 50 to extend through and pivot with respect to the washer 66'. As such, the angular relationship between the bone contacting surface 68' of the washer 66' and the longitudinal axis of the body 28 can vary in response to the entrance angle.

FIGS. 9-13 illustrate another embodiment of a bone fixation device 200 with an angularly adjustable proximal anchor 202. In this embodiment, similar reference numbers are used to identify components that are similar components described above.

The bone fixation device 200 comprises a body 28 that extending between a proximal end 30 and a distal end 32. The distal end 32 of the body is provide with a bone anchor 34 as described above. The illustrated body 28 is cannulated; however, it should be appreciated that in modified embodiments the body 28 can be solid. The proximal end of the anchor is provided with a hexagonal recess, which can be used in combination with a rotational tool to rotate the body 28. Of course, modified embodiments may use a variety of different male or female anti-rotational couplings.

The illustrated fixation device includes an annular flange 202 and proximal anchor 204. As with the proximal anchor described above, the proximal anchor 204 defines a housing 206 that is axially distally moveable along the body 28. Complementary locking structures 54, 58 on the housing 206 and the body 28 such as threads or ratchet like structures resist proximal movement of the anchor 204 with respect to the body 28 under normal use conditions. In some embodiments, the complementary locking structures 54, 48 may permit the anchor 204 to be axially advanced along the body 28 by rotation. In other embodiments, the complementary locking structures 54, 58 may permit the anchor 204 to be axially advanced along the body 24 without rotation. The illustrated proximal anchor 204 also includes a gap 205 such that the illustrated anchor 204 forms a split ring collar. In modified embodiments, the proximal anchor 204 can be formed without the gap 205.

The proximal anchor 204 preferably includes a smooth and more preferably rounded or spherical outer surface portion 208, which is configured to fit within a corresponding smooth and preferably rounded recessed portion 210 in the flange 202. As such, as shown in FIG. 12, when the proximal anchor 204 is positioned in the flange 202, the flange 202 resists distal movement of the proximal anchor 204 while permitting at least limited rotation of between the proximal anchor 204 and the flange 202. As such, the illustrate arrangement allows for angular movement of the flange 202 with respect to the anchor 204 to accommodate variable anatomical angles of the bone surface. In such applications, the flange 202 may seat directly against the outer surface of the ilium. Because the outer surface of the ilium is typically non-planar and/or the angle of insertion may not be perpendicular to the outer surface of the ilium, a fixed flange may contact only a portion of the outer surface of the ilium. This may cause the ilium to crack due to high stress concentrations. In contrast, the angularly adjustable flange 202 can rotate with respect to the body and thereby the bone contacting surface may be positioned more closely to the outer surface. More bone contacting surface is thereby utilized and the stress is spread out over a larger area. In addition, the flange 202, which has a larger diameter than the proximal anchor 50, effectively increases the shaft to head diameter of the fixation device, thereby increasing the size of the loading surface and reducing stress concentrations.

In the illustrated embodiment, the flange 202 includes a plurality of bone engagement features 212, which in the illustrated embodiment comprises one or more spikes 212 positioned on a contacting surface 216 of the flange 202. The spikes 212 provide additional gripping support especially when the flange 202 is positioned against, for example, uneven bone surfaces and/or soft tissue. However, it should be appreciated that in modified embodiments the flange 202 may be formed without the bone engagement features 212. Other structures for the bone engagement feature 212 may also be used, such as, for example, ridges, serrations etc. The illustrated embodiment also includes a tapered upper surface 214 that in certain embodiments may be flat.

Figure 14:
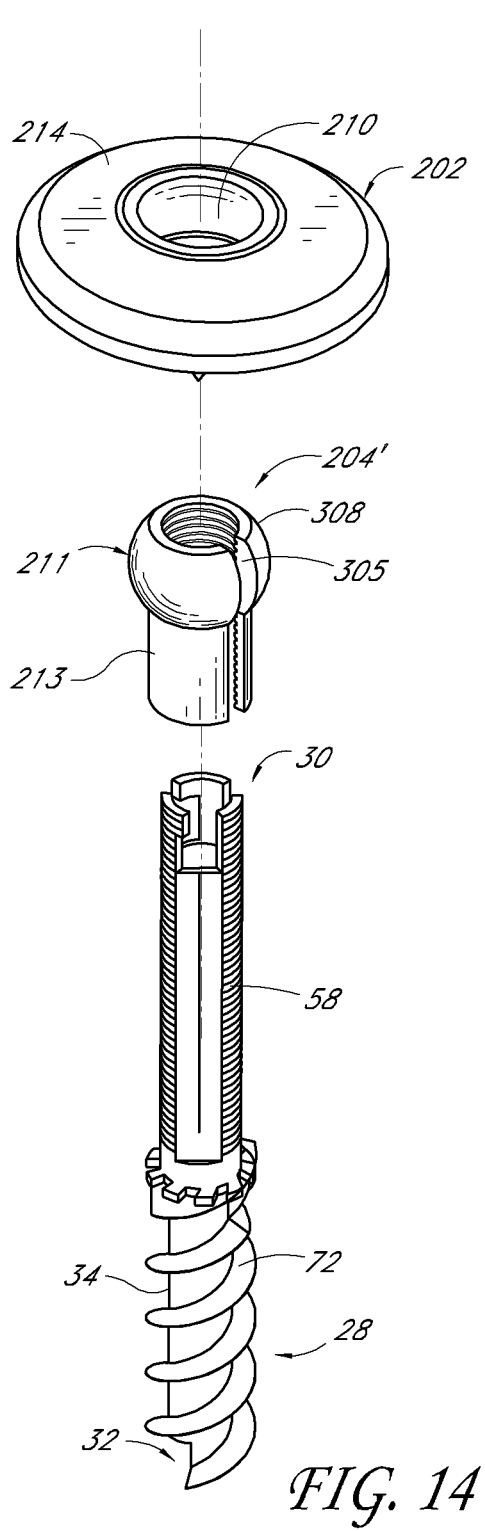
FIG. 14 is an unassembled side perspective view of another modified embodiment of a bone fixation device.
Figure 15:
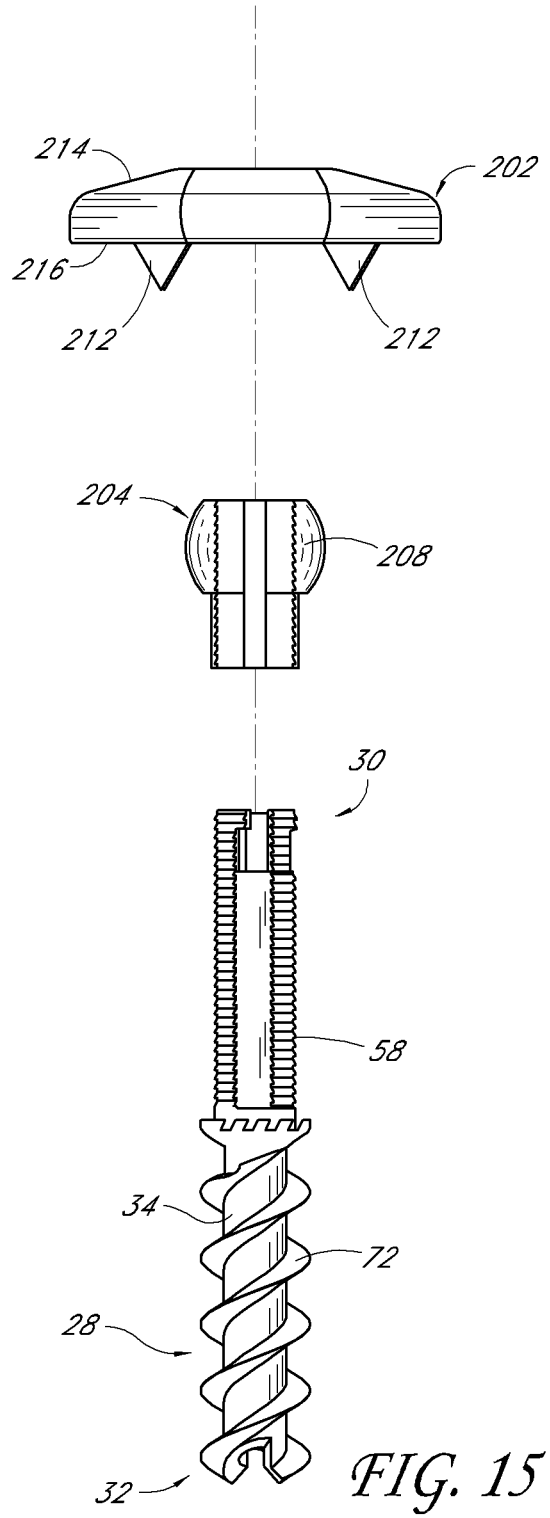
FIG. 15 is an unassembled side view of the bone fixation device of FIG. 9.

FIGS. 14 and 15 illustrate a modified embodiment of the angularity adjustable fixation device 200. In this embodiment, the proximal anchor 204' includes an upper portion 211 and a lower portion 213. The upper portion 211 is configured as described above with respect to the housing. The lower portion in the illustrated embodiment is generally tubular and a generally smaller diameter than the upper portion. The lower portion includes complementary retention structures 54 and generally provides the fixation device with a greater range of adjustable compression and additional retention structures as compared to the previous embodiment.

Figure 16A:
Figure 16B:
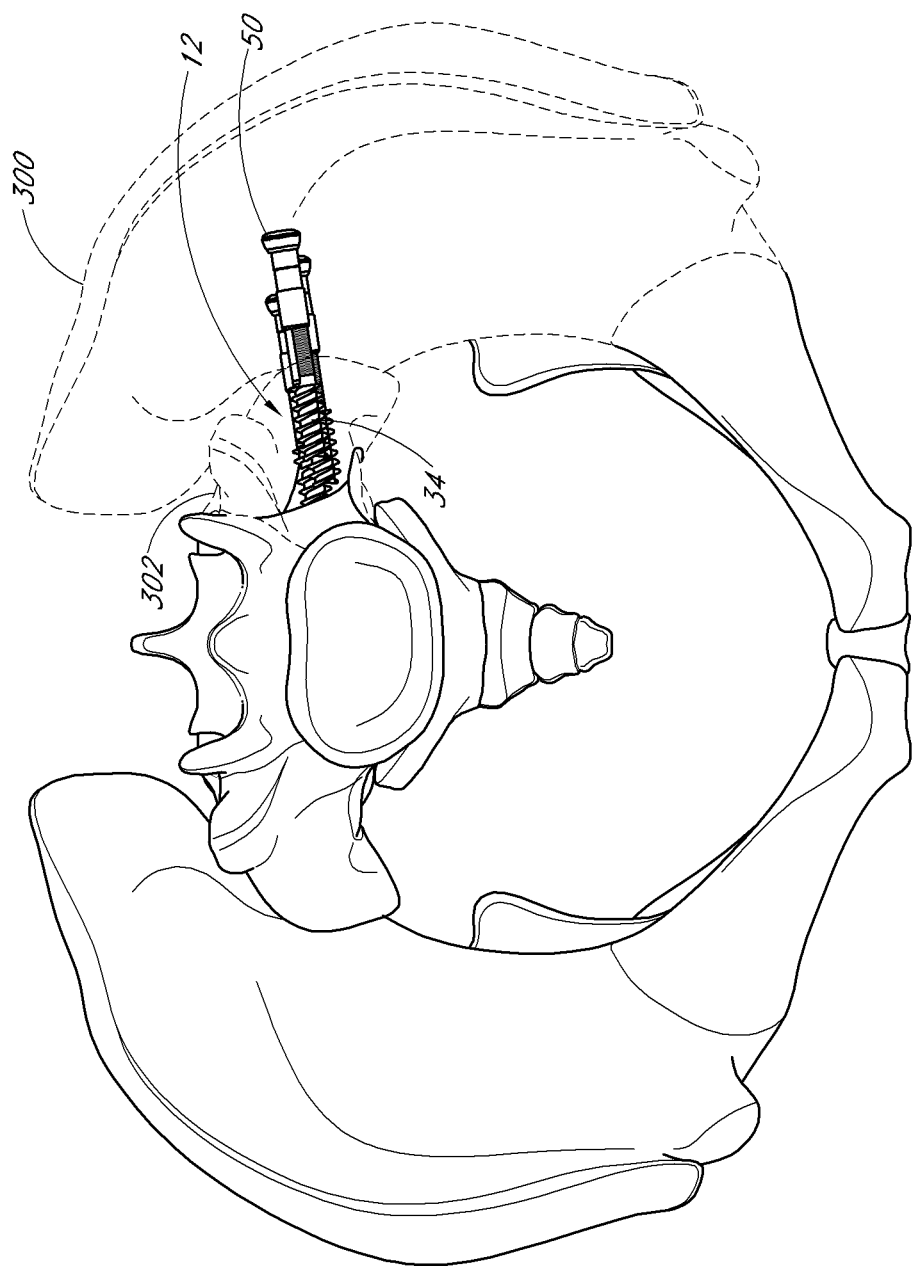
Figure 16C:
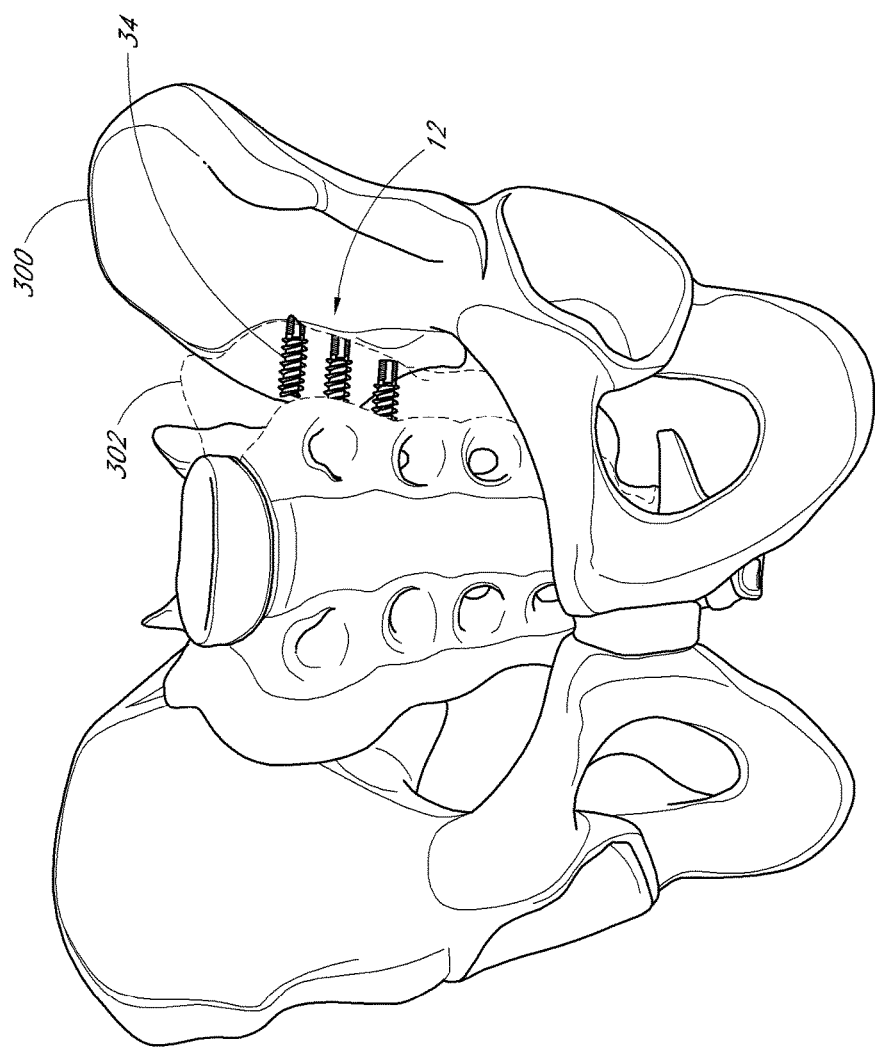
Figure 16D:
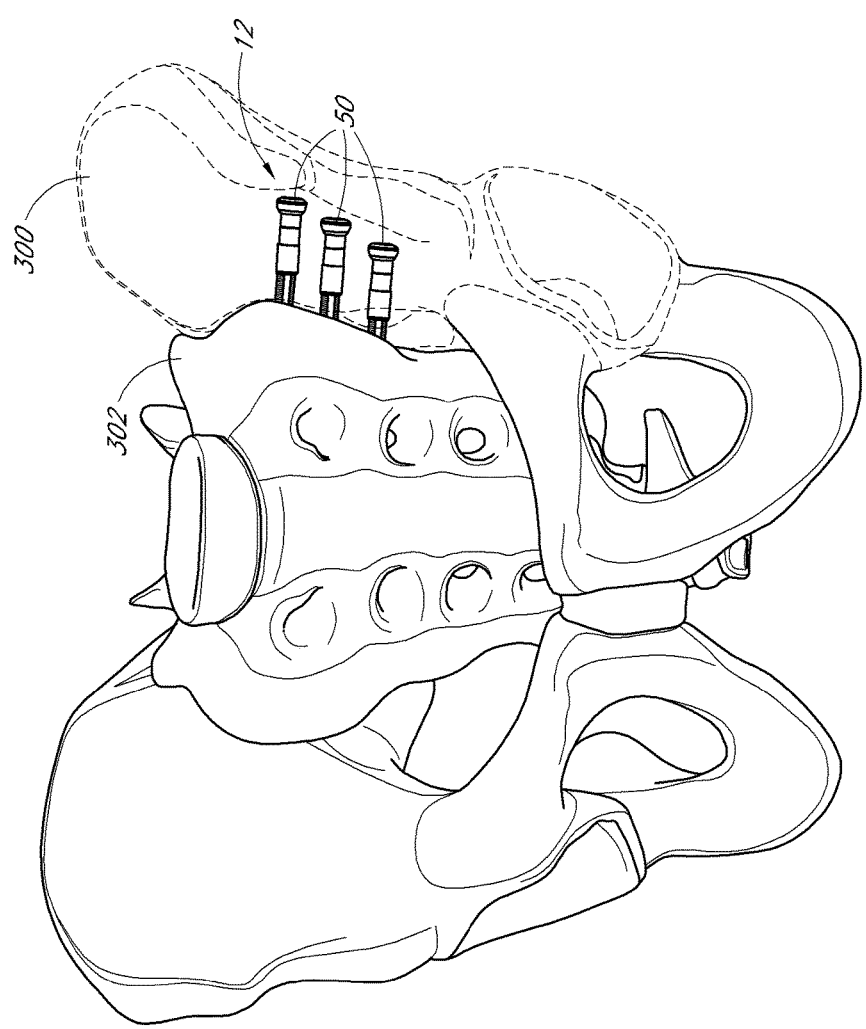
Figure 16E:
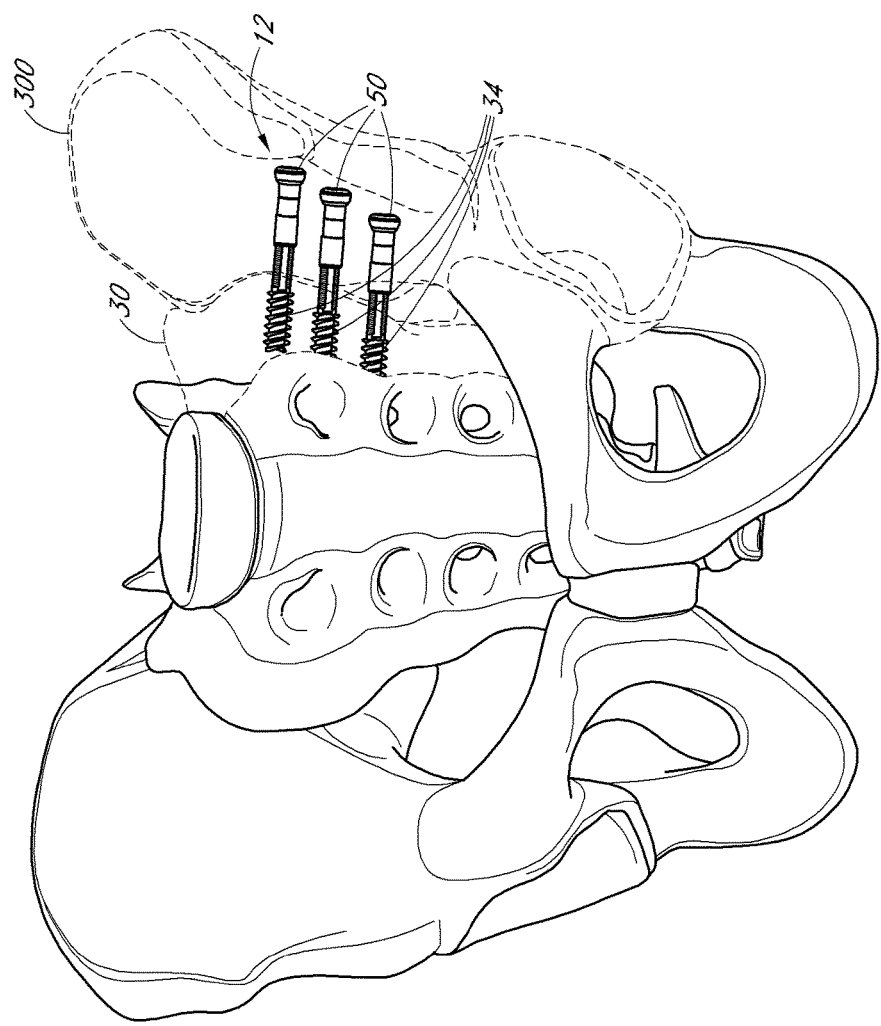
Figure 16G:
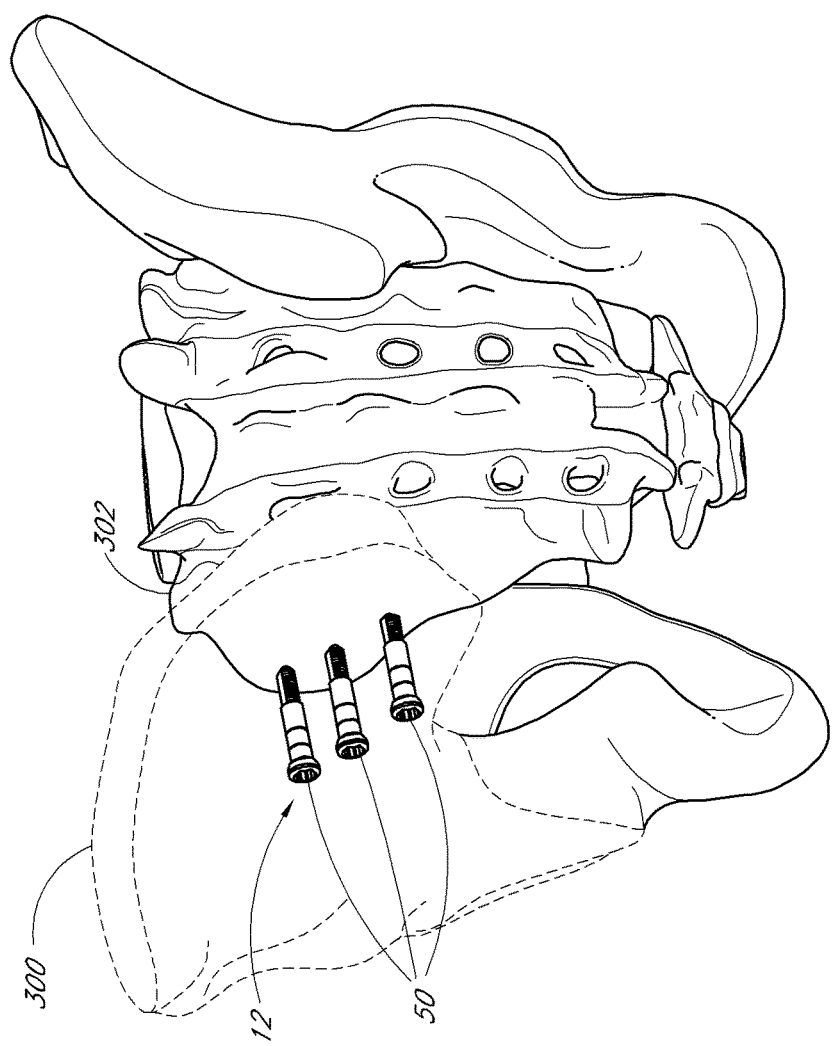
Figure 16H:
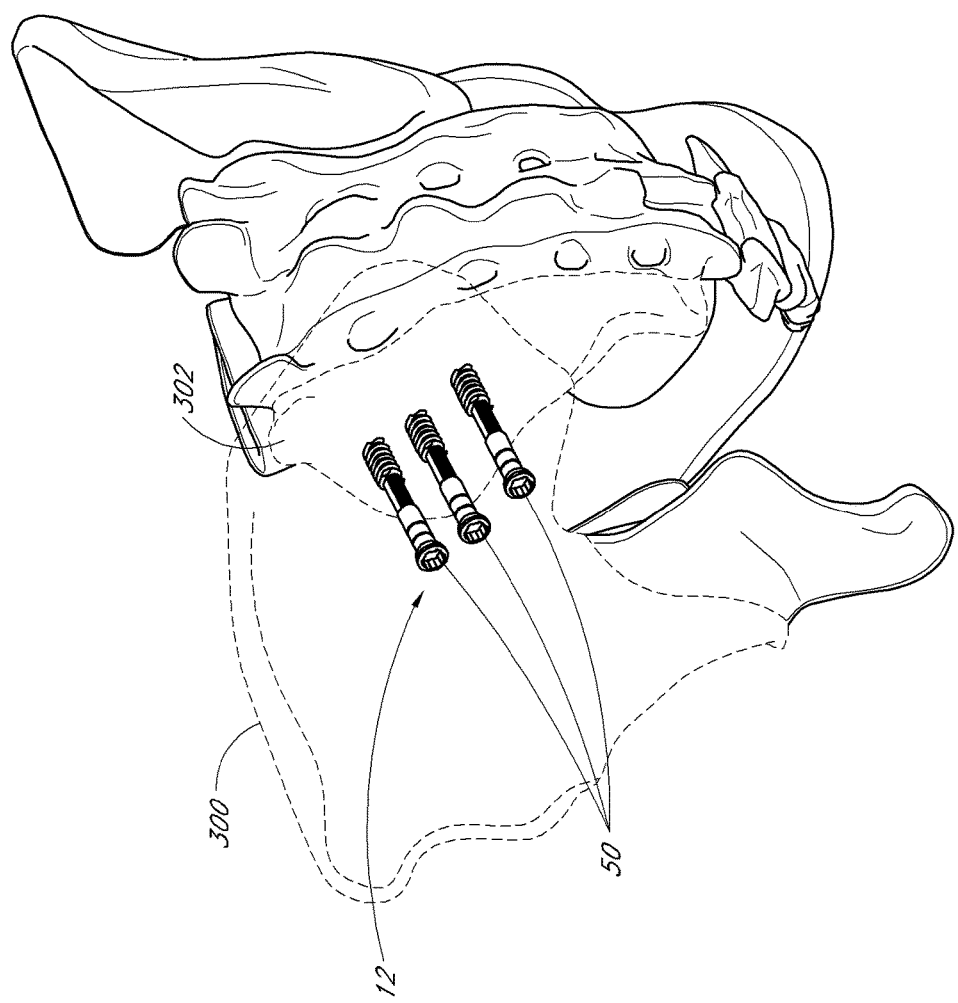

FIGS. 16A-H are various views of the pelvis and sacrum with the fixation device of FIG. 2 implanted therein. FIGS. 16A-B illustrate top views, while FIGS. 16C-E illustrate front views, and FIGS. 16F-H illustrate rear views. In some of these Figures, one or both of the ilium 300 and the sacrum 302 are illustrated as transparent, in order to more clearly identify the position of the fixation devices 12. In the illustrated embodiment, three fixation devices 12 are implanted. Each fixation device 12 is inserted through the ilium 300 and into the sacrum 302. The distal anchor 34 is disposed within the sacrum 302. Following implantation and compression, the proximal anchor 50 is disposed against the surface of the ilium 300. Although the illustrated embodiment utilizes three fixation devices 12, in other embodiments the number of devices can vary. For example, in some embodiments one fixation device can be employed, while in others two can be used. In various embodiments, three, four, or more fixation devices can be used.

In one embodiment of use, a patient with a sacroiliac joint instability is identified. The target entry point on the ilium 300 and a trajectory angle is then localized by intraoperative imaging, for example by fluoroscopy. A small incision is then made in the skin, and the tip of a guide wire or K-wire is driven through the soft tissue of the patient at an advantageous angle down to the target site on the ilium. The skin incision can then be lengthened, as necessary. In some embodiments, the incision may be lengthened to approximately 17 mm, for example. A similar incision can be made in the fascia, using the guide wire as the midpoint of the incision. A first dilator tube can then be passed over the guide wire until the tip of the dilator tube reaches the target point on the ilium 300. A second dilator tube having a larger diameter can then be passed over the first dilator tube. Advancing the second dilator tube to the target point on the ilium 300 further retracts tissue along the trajectory path. This can be repeated with additional dilator tubes, as necessary, with progressively wider dilator tubes to expand the patient's soft tissue down to the entry point on the ilium 300. An outer dilator tube, or cannula, is then left in place. A depth gauge may then be used to verify that the appropriate depth has been reached.

In some embodiments, a pre-drill can thereafter be advanced to the ilium 300, which is then verified by fluoroscopy. A drill can be advanced until it passes through the ilium and into the sacrum 302. The distal tip of a tap is driven into the sacrum until it reaches the appropriate depth, which can then be verified by fluoroscopy. A bone fixation device 12 is then driven through the ilium 300 and into the sacrum 302 until it reaches the appropriate depth, which can then also be verified by fluoroscopy. Once the distal anchor 34 is in the desired location, proximal traction is applied to the proximal end 30 of body 28, such as by conventional hemostats, pliers or a calibrated loading device, while distal force is applied to the proximal anchor. In this manner, the proximal anchor is advanced distally with respect to the body until the proximal anchor fits snugly against the outer surface of the ilium or a fixation plate/rod. Appropriate tensioning of the fixation device is accomplished by tactile feedback or through the use of a calibration device for applying a predetermined load on the implantation device. As explained above, one advantage of the structure of the illustrated embodiments is the ability to adjust compression independently of the setting of the distal anchor 34 within the sacrum. Appropriate stabilization of the sacroiliac joint can then be verified by fluoroscopy.

Following appropriate tensioning of the proximal anchor, the second portion 38 of the body 28 is preferably detached from the first portion 36 and removed. In the illustrated embodiment, this involves rotating the second portion 38 with respect to the first portion via the coupling 70. In other embodiments, this may involve cutting the proximal end of the body 28. For example, the proximal end of the body may be separated by cauterizing. Cauterizing may fuse the proximal anchor 50 to the body 32 thereby adding to the retention force between the proximal anchor 50 and the body 28. Such fusion between the proximal anchor and the body may be particularly advantageous if the pin and the proximal anchor are made from a bioabsorbable and/or biodegradable material. In this manner, as the material of the proximal anchor and/or the pin is absorbed or degrades, the fusion caused by the cauterizing continues to provide retention force between the proximal anchor and the body.

Following or before removal of the second portion 38 of each body 28, additional fixations devices may be implanted and/or additional stabilization implants (e.g., rods, plates, etc.) may be coupled to the body. The access site may be closed and dressed in accordance with conventional wound closure techniques.

In a modified arrangement, the second portion 38 may form part of the driving device, which is used to rotate the proximal anchor 50 and thus distal anchor 34 into the sacrum. The second portion 38 is used to apply proximal traction. After appropriate tensioning, the second portion 38 can be de-coupled from the first portion 36 and removed with the driving device.

In the foregoing variation, the second portion 38 may be connected to a rotatable control such as a thumb wheel on the deployment device. A container may be opened at the clinical site exposing the proximal end of the implant, such that the distal end of the second portion 38 may be removably coupled thereto. Proximal retraction of the hand tool will pull the implant out of its packaging. The implant may then be positioned within the aperture in the bone, rotated to set the distal anchor, and the hand piece may be manipulated to place proximal traction on the second portion 38 while simultaneously distally advancing the proximal anchor. Following appropriate tensioning, the second portion 38 may be disengaged from the implant, and removed from the patient. In the example of a threaded engagement, the second portion 38 may be disengaged from the implant by rotating a thumb wheel or other rotational control on the hand piece. In an alternate embodiment, such as where the second portion 38 comprises a pull wire, following appropriate tensioning across the joint, a first end of the pull wire is released such that the pull wire may be removed from the implant by proximal retraction of the second end which may be attached to the hand piece.

In some embodiments, the clinician will have access to an array of fixation devices 12, having, for example, different diameters, axial lengths and, if applicable, angular relationships. These may be packaged one or more per package in sterile or non-sterile envelopes or peelable pouches, or in dispensing cartridges which may each hold a plurality of devices 12. The clinician can assess the dimensions and load requirements, and select a fixation device from the array, which meets the desired specifications.

Myriad variations on the above-noted procedures can be used. For example, in some embodiments a dilator can be introduced directly, without the use of a guidewire. In some embodiments, a self-tapping high-speed drill can be used. The surgery may be performed percutaneously, minimally invasively, mini-open, or open, depending on surgeon preference.

The proximal anchor 50 may be carried by the fixation device 12 prior to advancing the body into the sacrum 302, or may be attached following placement of the body within the sacrum 302. In one embodiment, stabilization implants (e.g., a fixation plate and/or rod) may be placed over or coupled to the body or the proximal anchor before the proximal anchor is placed on the body.

As noted above, depending upon the sacroiliac joint fixation technique, the distal anchor of one or more bone fixation devices described herein are advanced through the ilium and into a suitable portion of the sacrum. In use, the threads of the fixation device can be placed across the sacroiliac joint, and compression achieved by distally advancing the proximal anchor. This approach not only provides compression across the sacroiliac joint which helps promote fusion, but also provides intraoperative flexibility to stop the distal anchor of the device where necessary and compress to the length to achieve an appropriate fit. The device may be used with or without a washer.

In the embodiment of FIGS. 16A-H, the proximal anchor is typically supported directly against the outer surface of the ilium 300. Because the outer surface is typically non-planar and/or the insertion angle of the fixation device is not perpendicular to the outer surface, an angularly adjustable flange may be used that can rotate with respect to the body and thereby the bone contacting surface may be positioned more closely to the outer surface of the ilium 300. This results in more bone contacting surface being utilized and the stress supported by the fixation device is spread out over a larger area of the ilium 300.

The surface of the fixation devices 12 may be treated to promote bone in-growth, and therefore fusion across the sacroiliac joint. These treatments may be placed over the entire length of the device or only on certain portions of the device depending on the specific needs it addresses or the advantages it provides. These treatments can include titanium plasma spray, a coating of hydroxyapatite, resorbable blast media, and others. In addition, bone graft (autogenous, demineralized bone matrix, bone morphogenetic protein, or other) may be be inserted into the pre-drilled hole prior to insertion of the fixation device. In some embodiments, an allograft sleeve may be placed over the fixation device so that the sleeve spans the sacroiliac joint, thereby encouraging bone in-growth and sacroiliac joint fusion.

Figure 17A:
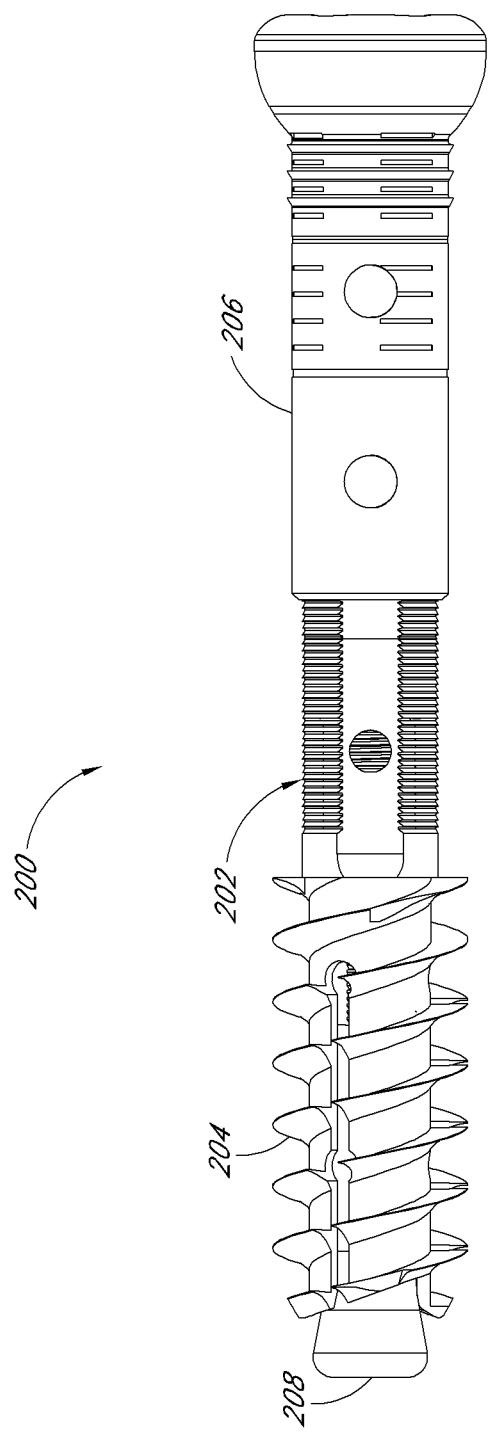
FIG. 17A shows a side view of an expandable bone fixation device in an unexpanded configuration.
Figure 17B:
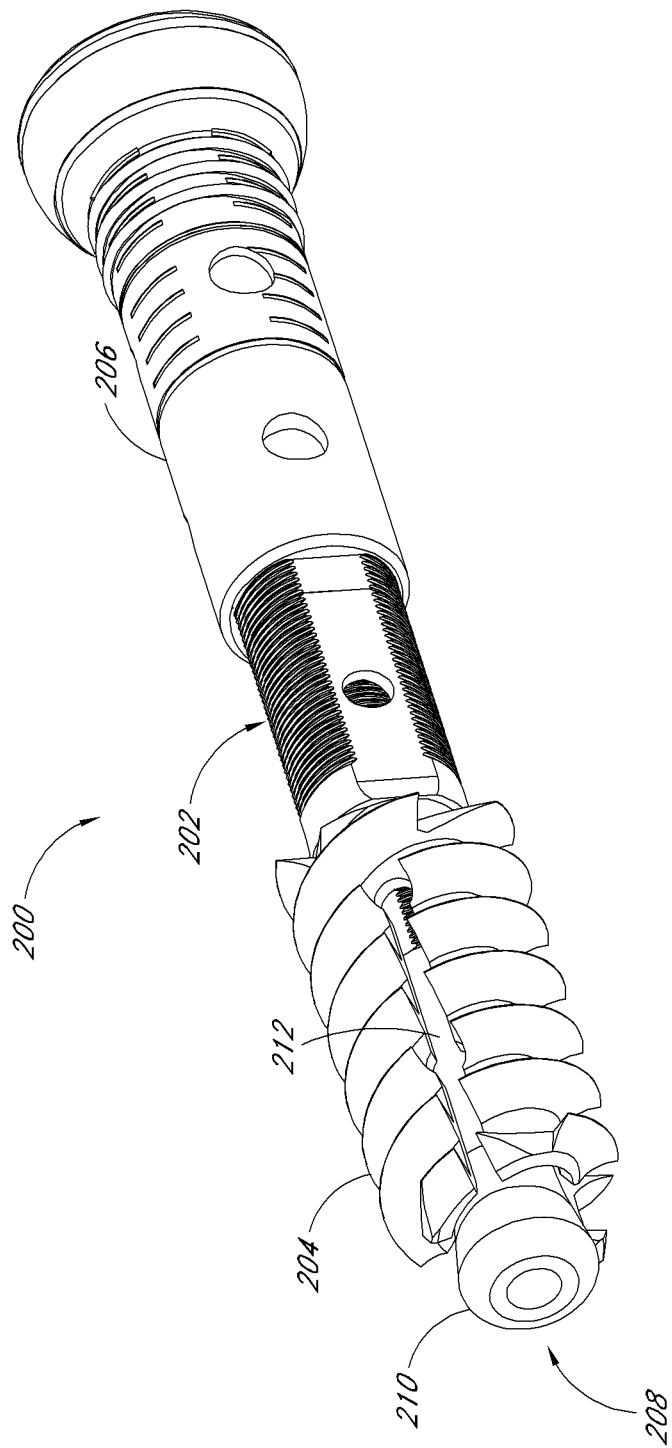
FIG. 17B shows a perspective view of the expandable bone fixation device of FIG. 17A.
Figure 17C:
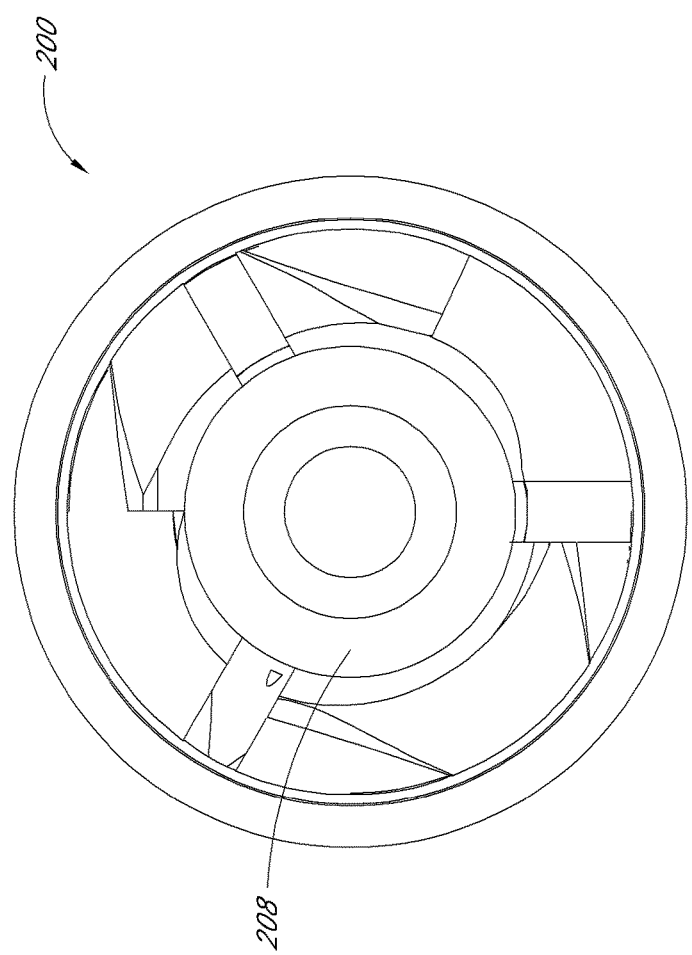
FIG. 17C shows a front view of the expandable bone fixation device of FIG. 17A.
Figure 17D:
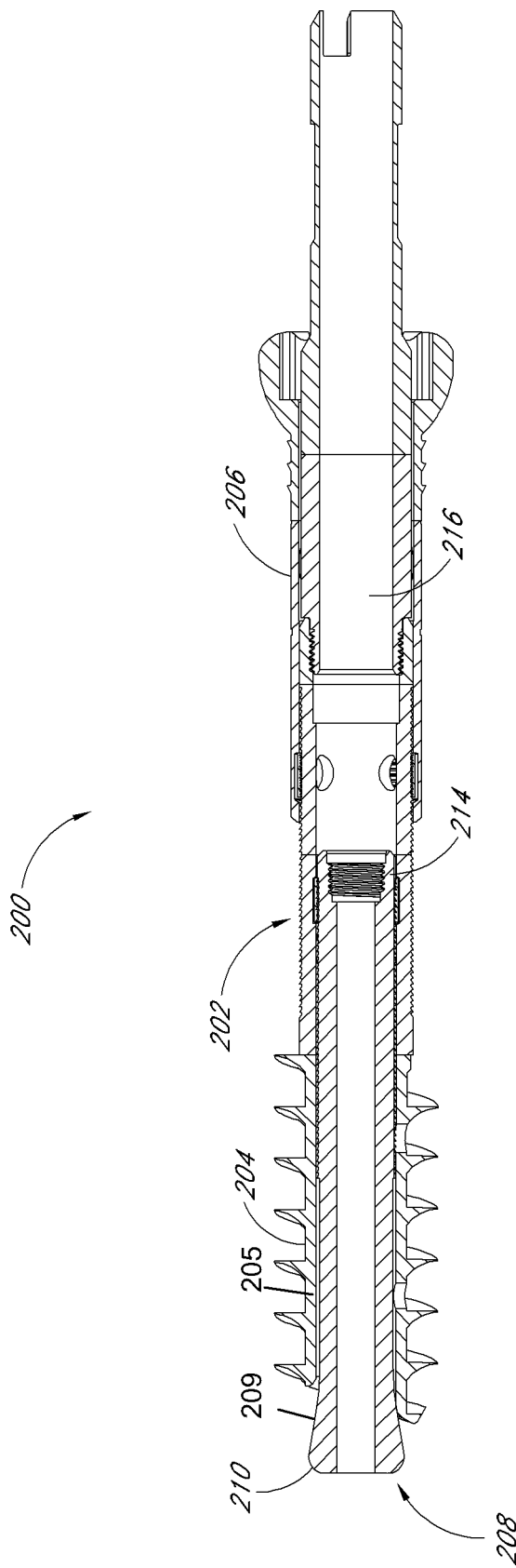
FIG. 17D shows a cross-sectional side view of the expandable bone fixation device of FIG. 17A.
Figure 17E:
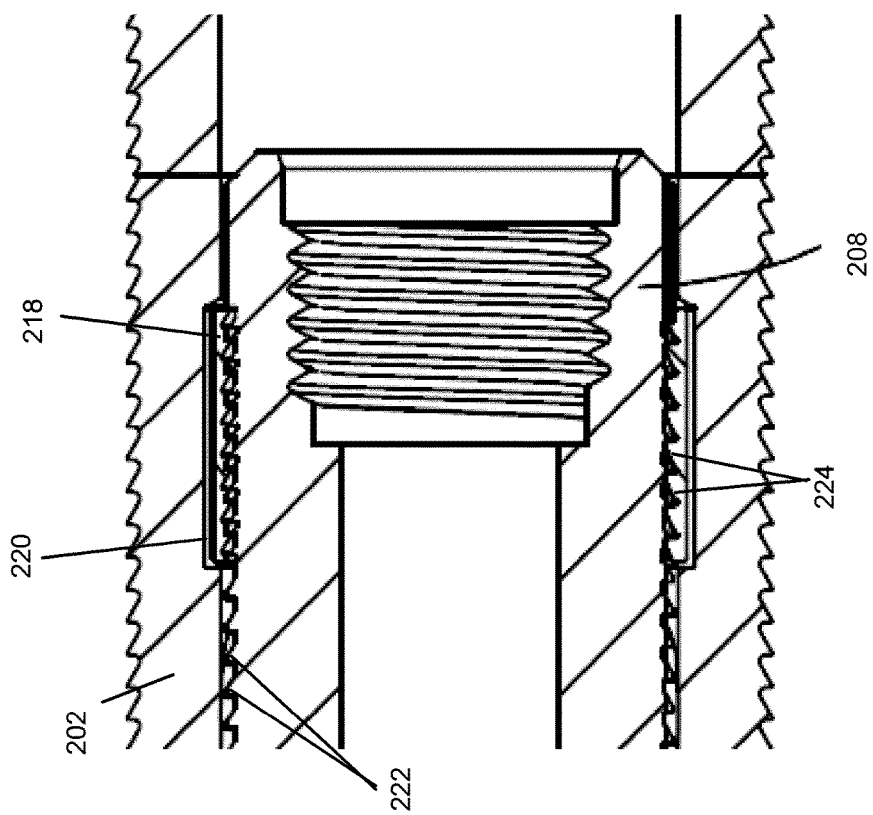
FIG. 17E shows an enlarged cross-sectional side view of the retention structure of the expandable fixation device of FIG. 17A.
Figure 18A:
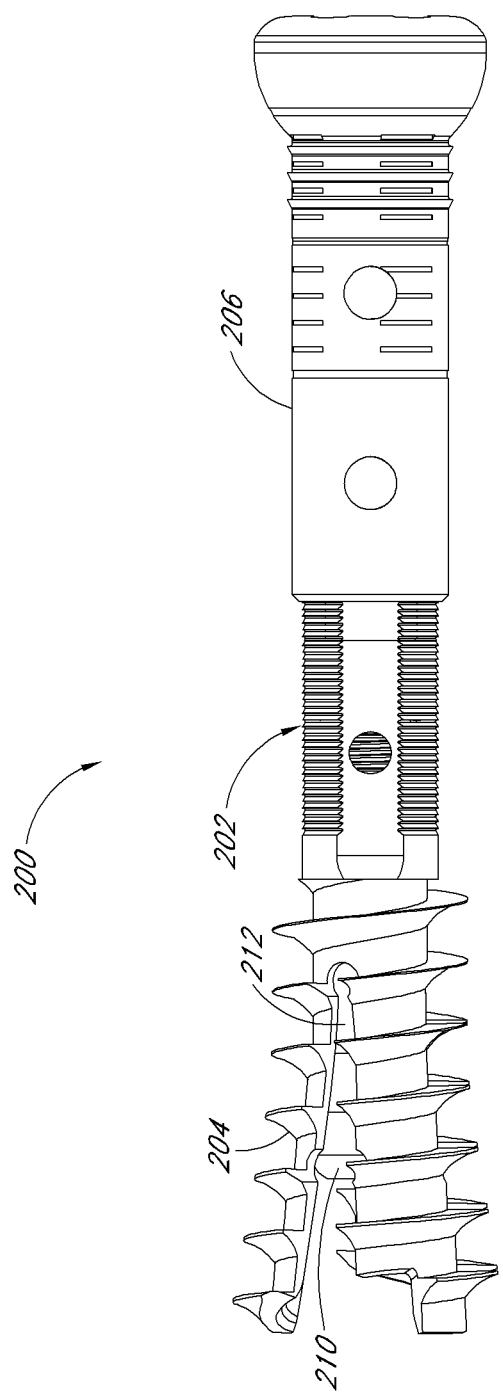
FIG. 18A shows a side view of an expandable bone fixation device in an expanded configuration
Figure 18B:
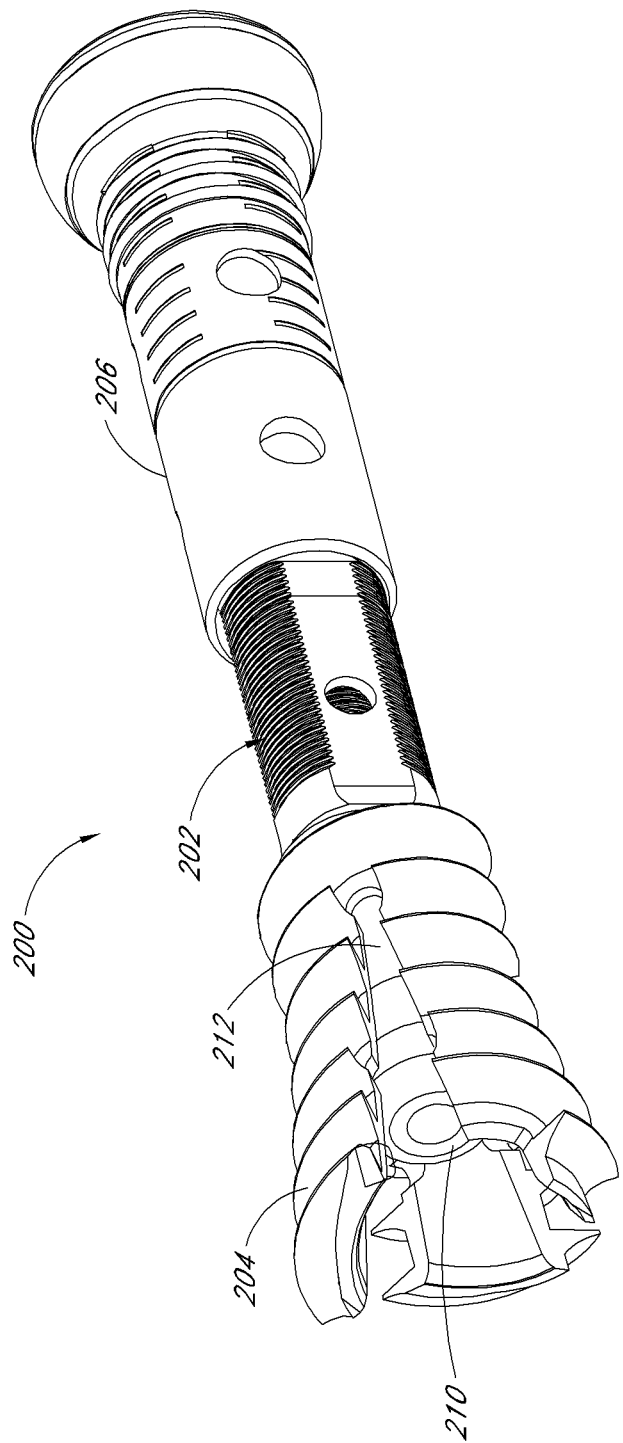
FIG. 18B shows a perspective view of the expandable bone fixation device of FIG. 18A.
Figure 18C:
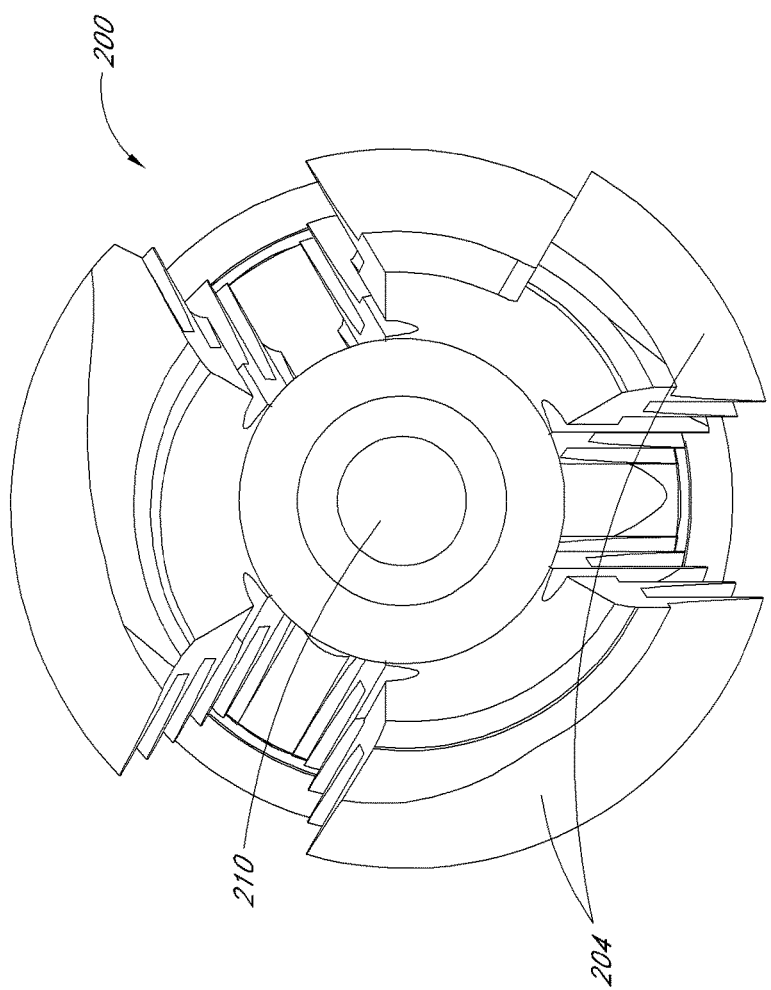
FIG. 18C shows a front view of the expandable bone fixation device of FIG. 18A.
Figure 18D:
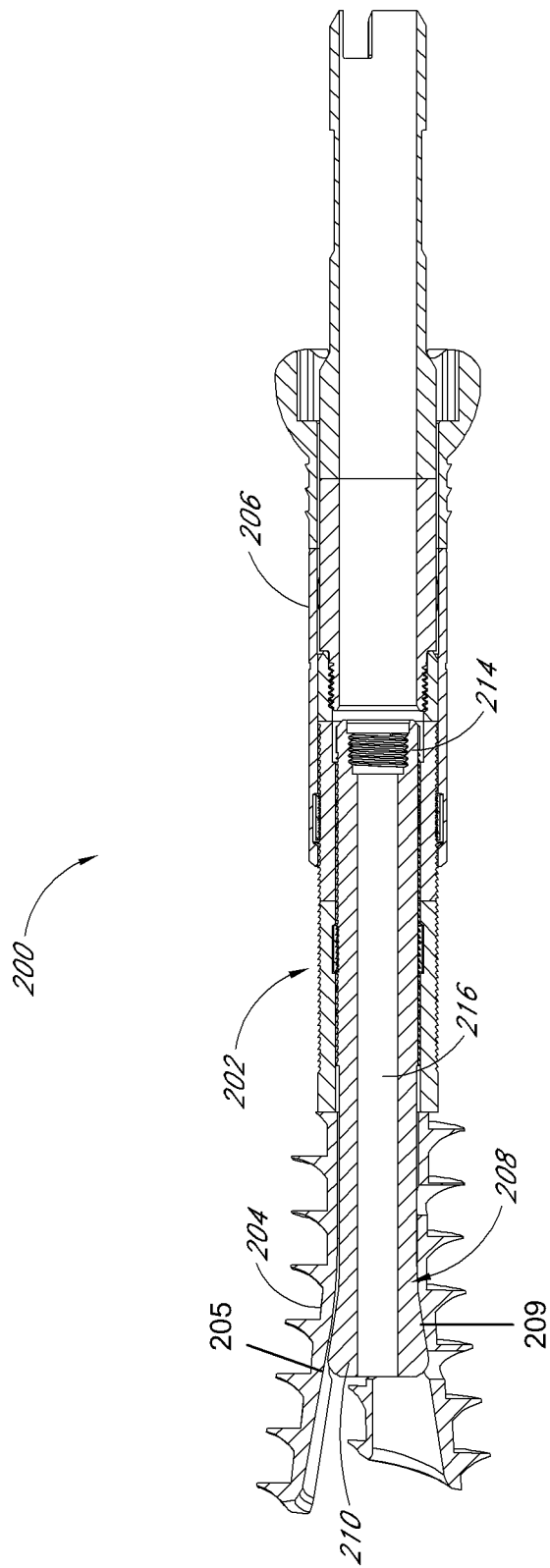
FIG. 18D shows a cross-sectional side view of the expandable bone fixation device of FIG. 18A.

FIG. 17A-D show side, perspective, front, and cross-sectional side views, respectively, of an embodiment of an expandable bone fixation device in an unexpanded configuration, with FIG. 17E showing an enlarged portion of the cross-sectional side view seen in FIG. 17D. FIGS. 18A-D show side, perspective, front, and cross-sectional side views, respectively, of an expandable bone fixation device in an expanded configuration. As illustrated, the fixation device 200 comprises an elongate body 202 having a distal anchor 204, which can be configured as described above. A separate proximal anchor 206 with complementary retention structures (e.g., as described above) can be advanced longitudinally along the length of the body 202 over retention structures of the body (e.g., as described above). Accordingly, as in the embodiments described above, the proximal anchor 206 can include features and elements described above to permit proximal movement of the elongate body 202 with respect to the proximal anchor 206 but to resist distal movement of the elongate body 202 with respect the proximal anchor 204. In this embodiment, an interior shaft 208 is disposed within an inner lumen of the elongate body 202. The expandable bone fixation device of FIGS. 17A-18D can be used in the techniques described above and/or features of the illustrated expandable bone fixation device can be combined with the embodiments of the bone fixation device described above.

As mentioned above, the bone fixation device 200 can function similar to the fixation devices described elsewhere herein, including distal advancement of the proximal anchor 206 over the retention structures of the elongate body 202 for secondary purchase, following insertion of the distal anchor 204 into bone. However, the bone fixation device 200, in the illustrated embodiment, can include additional functionality allowing for expansion (and accompanying additional purchase) of the distal anchor 204. In use, the distal anchor can be inserted into bone, for example into the sacrum. The interior shaft 208 can be disposed as illustrated in the unexpanded configuration of FIGS. 17A-E, with the tapered distal end 210 protruding from the distal end of the distal anchor 204. Once the distal anchor 204 is in position, the interior shaft 208 can be proximally retracted, upon which the outer surface 209 of the interior shaft 208 tapered distal end 210 abuts the inner surface 205 of the distal end of the anchor 204. As shown, the distal anchor 204 can include a plurality of slits 212, which can allow for flaring of the distal anchor upon contact with the tapered end 210 of the interior shaft 208. As illustrated in FIGS. 18A-D, the distal anchor 204 can flare, expanding radially and thereby provide additional purchase against bone. This additional purchase can be particularly advantageous in use with the soft bone in the sacrum.

In the illustrated embodiment, the inner member is proximally retracted to thereby flare the distal anchor. However, in other embodiments, the device can be configured such that the inner member can be advanced distally to cause flaring of the distal anchor. For example, the taper of the inner member may be configured to abut an angled surface interior to the distal anchor such that, upon distally moving the inner member, the tapered portion of the inner mamber contacts the angled surface of the distal anchor, causing flaring of the distal anchor as a result. Other such configurations are possible in which distal movement of the inner member causes the distal anchor to expand.

In some embodiments, proximal retraction of the interior shaft 208 can be accomplished by use of a pull pin (not shown), which can be inserted through the lumen of the elongate body 202 and threaded into the proximal end 214 of the interior shaft 208. Once the pull pin is engaged with the proximal end 214 via threading or other engagement mechanism, the interior shaft 208 can be proximally retracted. A retention structure (such as, for example, a ratchet mechanism) including a slip-ring (similar to that described above with respect to the proximal anchor) allows for retention of the interior shaft 208 in the proximally retracted position. In other embodiments, a modified complementary retention structures can be used, such as, for example, the various ratchet-like and threaded mechanisms described herein. Once the interior shaft 208 has been proximally retracted as desired, the pull pin can be disengaged from the proximal end of the interior shaft 208 (for example by unscrewing the engagement mechanism), and the pull pin can be removed from the device 200.

For example, as illustrated in FIG. 17E, the complementary retention structures can comprise an annular ring 218, which is positioned within an annular recess 220 formed in the elongate body 202. The inner surface of the annular ring 218 is complementary to ridges or threads 222 on the outer surface of interior shaft 208. The proximal portion of the annular recess 220 is sized and dimensioned such that as the interior shaft 208 is retracted proximally, the annular ring 218 can ride over the complementary retention structures 222 of the body 28. That is, the annular recess 220 provides a space for the annular ring 218 to move radially away from the interior shaft 208 as the interior shaft 208 is advanced distally. Preferably, the annular ring 218 is made from a material that provides sufficient strength and elasticity such as, for example, stainless steel or titanium. The annular ring 208 may be split such that it can be positioned over the interior shaft 208. In the illustrated embodiment, the annular ring 218 includes a plurality of teeth 224 although in modified embodiments the annular ring 218 may be formed without the teeth.

The recess 220 is also sized and dimensioned such that after the interior shaft 208 is appropriately positioned, the annular ring 218 becomes wedged between the interior shaft 208 a surface of the annular recess 220. In this manner, distal movement of the interior shaft 208 with respect to the elongate body 202 is prevented. Although not illustrated, it should be appreciated that in modified embodiments, the ring 218 can be formed without a gap. In some embodiments, the retention structure may also include features which assist in releasing the structure so that removal of the device is easier. For example, the annular ring can be based on threads so that the inner member can be rotated to advance forward, thereby collapsing the distal anchor that had been previously expanded. Other such mechanisms may likewise be used to assist in releasing the retention structure and thereby collapsing the flared distal anchor.

In some embodiments, bone graft of other material from within the interior lumen 216 of the bone fixation device 200 to the surrounding area outside of the bone fixation device by passing out the distal end 210 of the interior shaft 208.

In use, the device can accommodate bone graft through the assembly, as well as increasing the purchase with an expandable bone thread on the distal end, or both. The bone graft apertures could be holes or slots. In some embodiments, the graft material may also exit the additional apertures in the device so that bone graft (or other material) can be placed at advantageous locations such as directly at or into the joint or fracture. The inner member 208 may also have multiple apertures along its length to assist in bone graft exiting from varoius points along the device. The apertures may be various shapes, round, ovular, rectangular, etc.

In some embodiments, the device can have a very large and relatively sharp edged distal bone screw thread which works very well with the soft bone in the sacrum. With a larger screw assembly, the device can accommodate some geometry that will allow the injecting of bone graft thru it after it is in place (either before or after final compression). The device can also include holes and/or slots for the injection of bone graft or similar material. Additionally, as described above, the distal anchor can be flared out in-vivo. This option may greatly enhance the purchase in areas where bone density is less. The flaring action can easily be managed with a compression instrument or pull pin. So not only can a surgeon carefully and accurately position the distal end of the screw, she can dial in distal flare/purchase as well as the amount of secondary compression by compressing the collar. In some embodiments, a washer can be used to slip on prior to inserting the screw, as described elsewhere herein.

In one embodiment of use, a patient with a sacroiliac joint instability is identified, and a drill can be advanced until it passes through the ilium and into the sacrum. The distal tip of a tap is driven into the sacrum until it reaches the appropriate depth, which can then be verified by fluoroscopy. An expandable bone fixation device 200 is then driven through the ilium and into the sacrum until it reaches the appropriate depth, which can then also be verified by fluoroscopy. Once the distal anchor 204 is in the desired location, proximal traction can be applied to the proximal end 204 of elongate body 202, such as by conventional hemostats, pliers or a calibrated loading device, while distal force is applied to the proximal anchor 206. In this manner, the proximal anchor 206 is advanced distally with respect to the elongate body 202 until the proximal anchor 206 fits snugly against the outer surface of the ilium or a fixation plate/rod. A pull pin or rod may then be inserted into the device 200 and coupled with the inner member 210, after which the inner member 210 can be proximally retracted with respect to the distal anchor 204. Proximal retraction of the inner member 210 causes the distal anchor 204 to flare, thereby increasing purchase within the sacrum. In some embodiments, the distal anchor 204 may be flared before the proximal anchor 206 is advanced distally with respect to the elongate body 202. The pull pin may then be removed, and additional fixation devices may be implanted and/or additional stabilization implants may be coupled to the elongated body. The access site may be closed and dressed in accordance with conventional wound closure techniques.

Although embodiments described above are directed to stabilization of the sacroiliac joint, in various embodiments an expandable bone anchor may be used in other applications, for example various orthopedic or spinal applications, pedicle screws, etc. In some embodiments, the expandable bone anchor may include a flaring distal anchor but may omit a proximal anchor.

In various embodiments, bone graft material (e.g., autograft, allograft, demineralized bone matrix), bone growth promoters (e.g., bone morphogenic proteins), and/or bone cement may be used in conjunction with the fixation devices described herein. For example, bone graft material, bone growth promoters, and/or bone cement can be introduced into the sacroiliac joint before and/or after insertion of the fixation device(s) across the joint. This may help promote fusion of the joint, and/or to increase fixation. This can be particularly advantageous in cases in which the bone quality is poor, but the approach may be applied to any quality of bone. In some embodiments, the fixation device is cannulated. Accordingly, in such embodiments the bone graft, bone growth promoters, and/or bone cement can be introduced through the interior passageway after insertion of the fixation device. In some embodiments, the fixation device may be cannulated and may also include a plurality of exit holes. For example, a plurality of exit holes may be arranged on the outer surface of the fixation device. The exit holes may be in fluid communication with the interior passageway, such that bone graft material, bone growth promoters, and/or bone cement introduced through the interior passageway can exit through the plurality of exit holes. In some embodiments, one or more of the exit holes may be oriented in a direction transverse to the interior passageway. In some embodiments, the exit holes may be distributed along substantially the entire length of the fixation device. In other embodiments, the exit holes may be limited to one or more regions of the fixation device. For example, the exit holes may be limited to certain regions such that the bone graft material, bone growth promoters, and/or bone cement exits the fixation device in preferential areas to promote fusion, such as at the joint. In some embodiments, the exit holes may be limited to the distal region, such that the exiting bone graft material, bone growth promoters, and/or bone cement improves fixation.

The fixation devices described above may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful: 1) the blend of poly(p-dioxanone) and a lactide/glycolide copolymer, as disclosed in U.S. Pat. No. 4,646,741 which is incorporated by reference and (2) the glycolide-rich blend of two or more polymers, one polymer being a high lactide content polymer, and the other being a high glycolide content disclosed in U.S. Pat. No. 4,889,119 which is incorporated by reference. Additional bioabsorbable materials are disclosed in copending application Ser. No. 09/558,057 filed Apr. 26, 2000, the disclosure of which is incorporated in its entirety herein by reference.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the invention (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

The terms "approximately", "about", and "substantially" as used herein represent an amount or characteristic close to the stated amount or characteristic that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount or characteristic. The term "up to about" as used herein has its ordinary meaning as known to those skilled in the art and may include 0 wt. %, minimum or trace wt. %, the given wt. %, and all wt. % in between.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

In the embodiments described above, it should be appreciated that the distal anchor may be configured to be used with a pre-drilled hole and/or self tapping.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

We claim:

1. A bone fixation device, comprising:
   an elongate body, having a proximal end and a distal end;
   a distal anchor on the distal end, the distal anchor defining a plurality of slits and configured to purchase with bone;
   a retention structure on the elongate body, proximal to the distal anchor;
   a proximal anchor, moveably carried by the elongate body;
   at least one complementary retention structure on the proximal anchor configured to permit proximal movement of the elongate body with respect to the proximal anchor but to resist distal movement of the elongate body with respect the proximal anchor; and
   an inner member disposed within the elongate body, the inner member comprising a distal end configured to abut the distal anchor when proximally retracted,
   wherein the distal anchor is configured to flare outwardly upon proximal movement of the inner member so as to further purchase with the bone, and the outwardly flared portion of the distal anchor defines an internal space, and
   wherein the inner member defines a lumen extending from a proximal end of the inner member to the distal end of the inner member, the lumen being open to the internal space when the inner member is proximally retracted.

2. The bone fixation device of claim 1, wherein the distal end of the inner member is tapered.

3. The bone fixation device of claim 1, wherein the distal anchor comprises a helical flange having the plurality of slits formed therein.

4. The bone fixation device of claim 1, wherein the distal anchor is configured to be advanced through a bore in the ilium and into the sacrum.

5. The bone fixation device of claim 1, wherein the proximal anchor comprises a tubular housing.

6. The bone fixation device of claim 1, wherein the proximal anchor defines a longitudinal axis, the bone fixation device further comprises a flange configured to receive the proximal anchor, the flange defines a longitudinal axis, and the proximal anchor and the flange have complementary surface structures to permit angular adjustment with respect to the longitudinal axis of the proximal anchor and the elongate body and the longitudinal axis of the flange.

7. The bone fixation device of claim 6, wherein the complementary surface structures of the proximal anchor and the flange comprise a spherical outer surface of the proximal anchor and a corresponding spherical recess in the flange.

8. The bone fixation device of claim 1, wherein the elongate body has a length of between about 30 mm and about 120 mm.

9. The bone fixation device of claim 1, wherein the elongate body has a maximum diameter of between about 3 mm and about 12 mm.

10. The bone fixation device of claim 1, wherein the elongate body comprises an interior passageway in fluid communication with at least one exit hole and the lumen of the inner member.

11. The bone fixation device of claim 10, wherein the elongate body comprises a plurality of exit holes in fluid communication with the interior passageway.

12. The bone fixation device of claim 1, wherein the elongate body comprises an annular ring with at least one retention structure corresponding to at least one complementary retention structure on the inner member.

13. A method of providing bone fixation, comprising the steps of:
    positioning a fixation device against a bone, the fixation device comprising a body having a distal anchor, a proximal anchor, and an inner member disposed within the body;
    advancing the distal anchor of the fixation device into the bone so as to cause the distal anchor to purchase with the bone;
    axially shortening the fixation device by reducing a distance between the distal anchor and the proximal anchor, such that a locking element on the proximal anchor engages at least one retention structure on the body; and
    proximally retracting the inner member to cause the distal anchor to flare outwardly so as to cause the distal anchor to additionally purchase with the bone, wherein the inner member defines a lumen that is open with an interior passageway of the body before and after the proximally retracting step.

14. The method of claim 13, wherein axially shortening the fixation device comprises axially advancing the proximal anchor without rotating the proximal anchor with respect to the body.

15. The method of claim 13, wherein the bone comprises an ilium, and wherein advancing the distal anchor comprises advancing the distal anchor through a bore in the ilium and into a sacrum.

16. The method of claim 15, wherein axially shortening the fixation device and proximally retracting the inner member apply compression between the sacrum and the ilium.

17. The method of claim 16, further comprising introducing bone graft material, bone growth promoters, and/or bone cement into the sacroiliac joint through the interior passageway and the lumen.

18. The method of claim 13, wherein the body has a length of between about 30 mm and about 120 mm.

19. The method of claim 13, wherein the body has a maximum diameter of between about 3 mm and about 12 mm.

20. The method of claim 13, wherein the distal anchor comprises a helical flange having a plurality of slits formed therein.

21. The method of claim 13, wherein the step of proximally retracting the inner member comprises advancing a slip ring over retention structures on the inner member.

22. The method of claim 13, wherein the step of proximally retracting the inner member is performed before the step of axially shortening the fixation device.

23. A bone fixation device, comprising:
- an elongate body having a proximal end, a distal end, and a distal anchor on the distal end, the distal anchor defining slits and configured to purchase with bone;
- a retention structure on the elongate body and located proximal to the distal anchor, the elongate body defining a lumen extending from the proximal end to the distal end of the elongate body, the lumen including a retention structure;
- a proximal anchor, moveably carried by the elongate body;
- at least one complementary retention structure on the proximal anchor configured to engage the retention structure on the elongate body so as to permit proximal movement of the elongate body with respect to the proximal anchor but to resist distal movement of the elongate body with respect the proximal anchor; and
- an inner member moveably disposed within the lumen of the elongate body, the inner member comprising a distal end configured to radially expand the distal anchor when proximally retracted relative to the distal anchor so as to cause the distal anchor to further purchase with the bone, the inner member including a complementary retention structure configured to engage the retention structure of the lumen to permit proximal movement of the inner member with respect to the elongate body but to resist distal movement of the inner member with respect the elongate body, the inner member defining a second lumen extending from a proximal end of the inner member to the distal end of the inner member, the second lumen in communication with the lumen of the elongate body for conveyance of a material therethrough.

* * * * *